(12) United States Patent
Weiner et al.

(10) Patent No.: US 10,155,795 B2
(45) Date of Patent: Dec. 18, 2018

(54) COMPOSITIONS COMPRISING HYPOXIA INDUCIBLE FACTOR-1 ALPHA AND METHODS OF USING THE SAME

(71) Applicants: David B. Weiner, Merion, PA (US); Karuppiah Muthumani, Cherry Hill, NJ (US); Emile Mohler, Radnor, PA (US); Geoffrey Ouma, Newark, DE (US)

(72) Inventors: David B. Weiner, Merion, PA (US); Karuppiah Muthumani, Cherry Hill, NJ (US); Emile Mohler, Radnor, PA (US); Geoffrey Ouma, Newark, DE (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/776,516

(22) PCT Filed: Mar. 14, 2014

(86) PCT No.: PCT/US2014/029263
§ 371 (c)(1),
(2) Date: Sep. 14, 2015

(87) PCT Pub. No.: WO2014/144731
PCT Pub. Date: Sep. 18, 2014

(65) Prior Publication Data
US 2016/0031956 A1 Feb. 4, 2016

Related U.S. Application Data

(60) Provisional application No. 61/800,703, filed on Mar. 15, 2013.

(51) Int. Cl.
| | | |
|---|---|---|
| C07H 21/04 | (2006.01) |
| C12N 15/09 | (2006.01) |
| C12N 15/11 | (2006.01) |
| C12N 15/63 | (2006.01) |
| A61P 9/10 | (2006.01) |
| C07K 14/47 | (2006.01) |
| A61K 38/17 | (2006.01) |
| A61K 39/00 | (2006.01) |
| A61K 41/00 | (2006.01) |
| A61N 1/32 | (2006.01) |
| A61K 48/00 | (2006.01) |

(52) U.S. Cl.
CPC ...... *C07K 14/4702* (2013.01); *A61K 38/1709* (2013.01); *A61K 39/0005* (2013.01); *A61K 41/0047* (2013.01); *A61K 48/005* (2013.01); *A61N 1/327* (2013.01); *A61P 9/10* (2018.01); *C07H 21/04* (2013.01); *C12N 15/09* (2013.01); *C12N 15/11* (2013.01); *C12N 15/63* (2013.01); *A61K 2039/53* (2013.01)

(58) Field of Classification Search
None
See application file for complete search history.

(56) References Cited

U.S. PATENT DOCUMENTS

| | | |
|---|---|---|
| 2003/0045686 A1 | 3/2003 | Kaelin, Jr. et al. |
| 2011/0319479 A1 | 12/2011 | Breitbart et al. |
| 2012/0107297 A1 | 5/2012 | Im et al. |

FOREIGN PATENT DOCUMENTS

| | | |
|---|---|---|
| CN | 20071164320 | 11/2008 |
| JP | 2005508607 A | 9/2002 |
| JP | 2009545310 A | 2/2008 |
| JP | 2009001521 A | 1/2009 |
| JP | 2011516070 A | 10/2009 |
| WO | 02074980 A2 | 9/2002 |
| WO | 2008015675 A2 | 2/2008 |
| WO | 2009124312 A2 | 10/2009 |
| WO | 2011130566 A2 | 10/2011 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Iyer et al., 1998, "The Human Hypoxia-Inducible Factor 1alpha Gene:HIF1AStructure and Evolutionary Conservation", Genomics 52, Article No. GE985416, pp. 159-165.
Bosch-Marce et al., 2007, "Effects of Aging and Hypoxia-Inducible Factor-1 Activity on Angiogenic Cell Mobilization and Recovery of Perfusion After Limb Ischemia", Circ. Res., vol. 101, No. 12, pp. 1310-1318.
Kim et al., "Failure to prolyl hydroxylate hypoxia-inducible factor alpha phenocopies VHL inactivation in vivo" EMBO J 25(19):4650-62, Sep. 14, 2006.
Nishikage et al., "In Vivo Electroporation Enhances Plasmid-Based Gene Transfer of Basic Fibroblast Growth Factor for the Treatment of Ischemic Limb," Journal of Surgical Research, 2004, 120:37-46.

* cited by examiner

*Primary Examiner* — Zachary C Howard
(74) *Attorney, Agent, or Firm* — Riverside Law LLP

(57) ABSTRACT

Disclosed herein is a therapeutic comprising hypoxia inducible factor-1 alpha (HIF-1α). Also disclosed herein is a method for treating hypoxia or ischemia in a subject in need thereof. The method may comprise administering the vaccine to the subject in need thereof.

12 Claims, 15 Drawing Sheets
Specification includes a Sequence Listing.

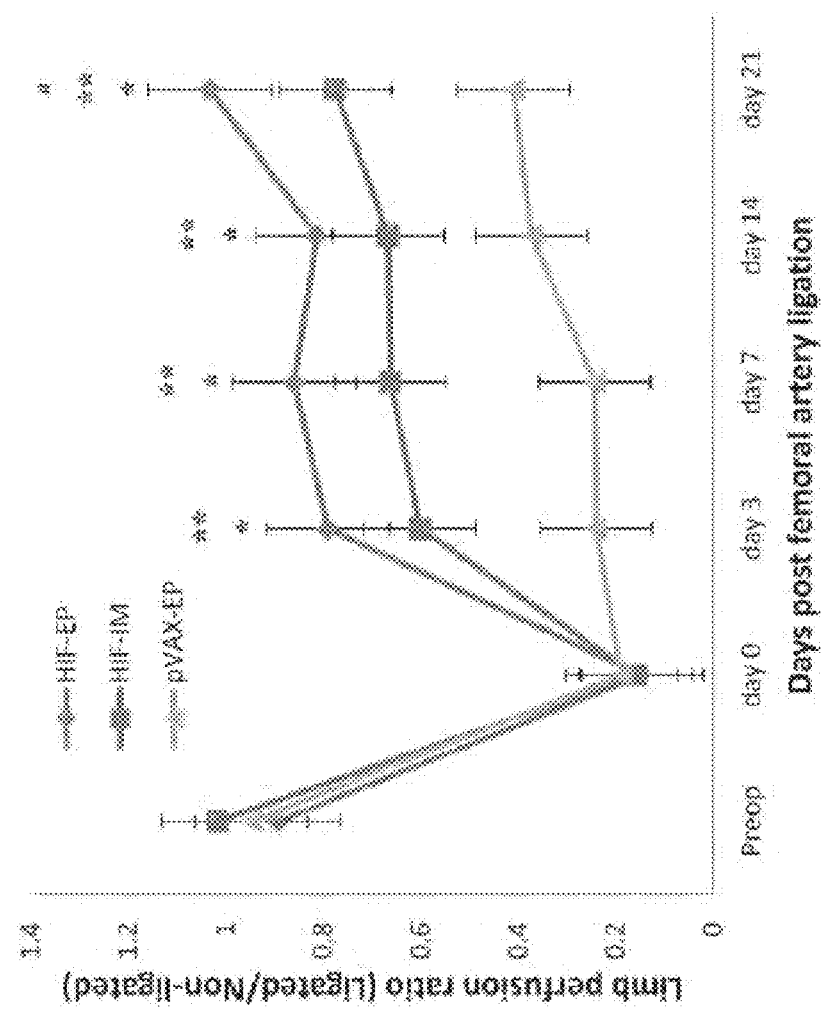
FIG. 3 (con't)

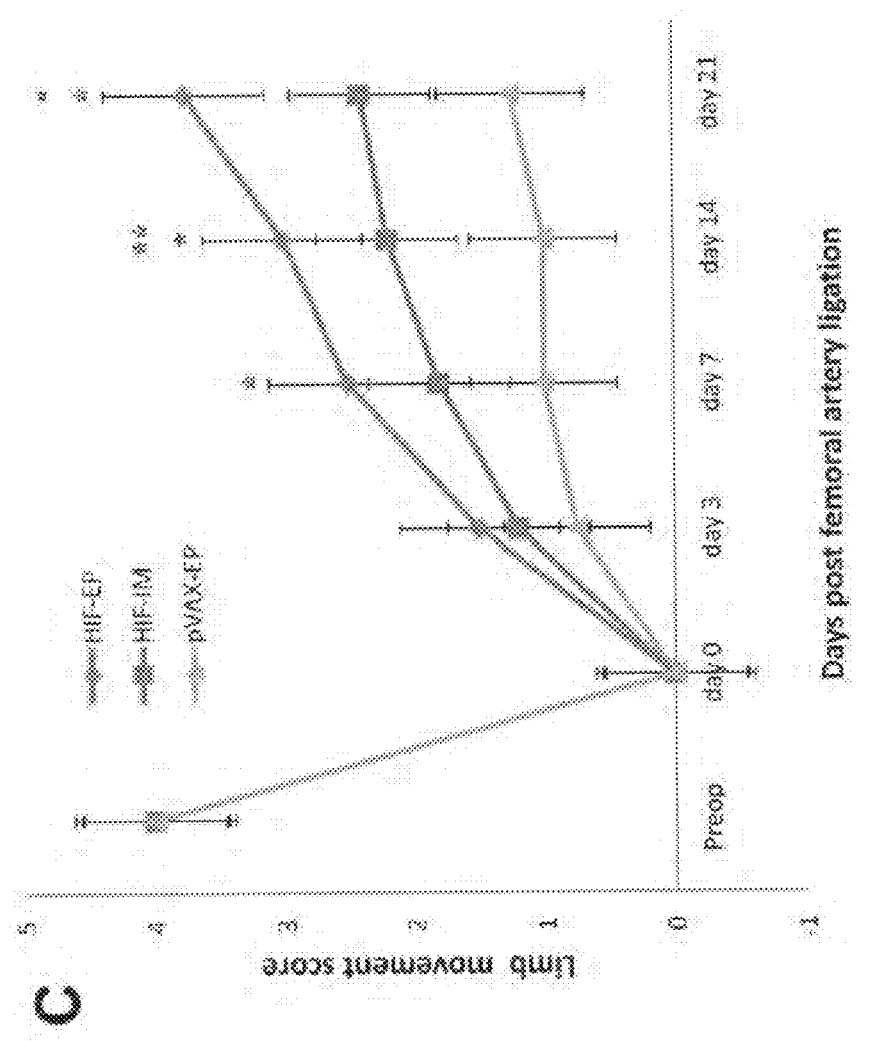
FIG. 3 (con't)

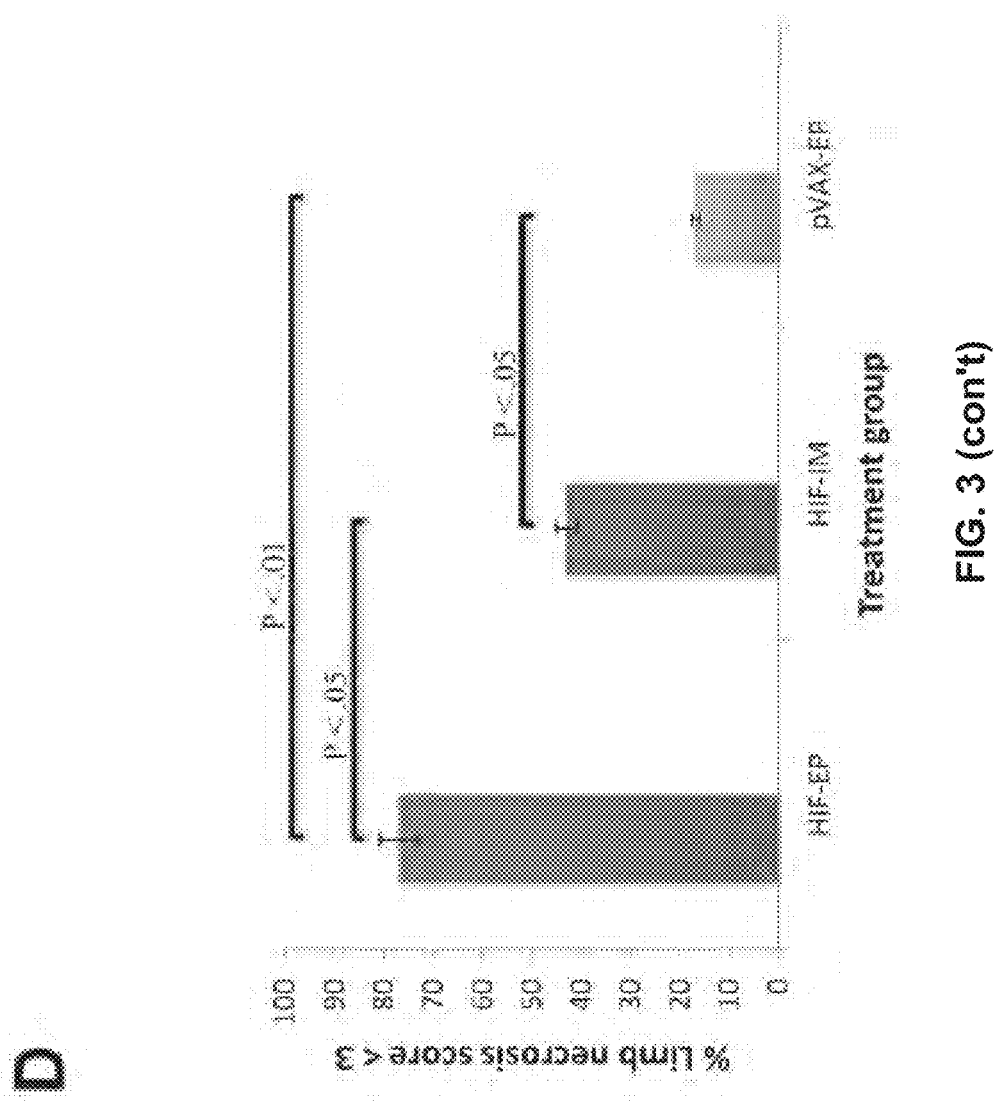
FIG. 3 (con't)

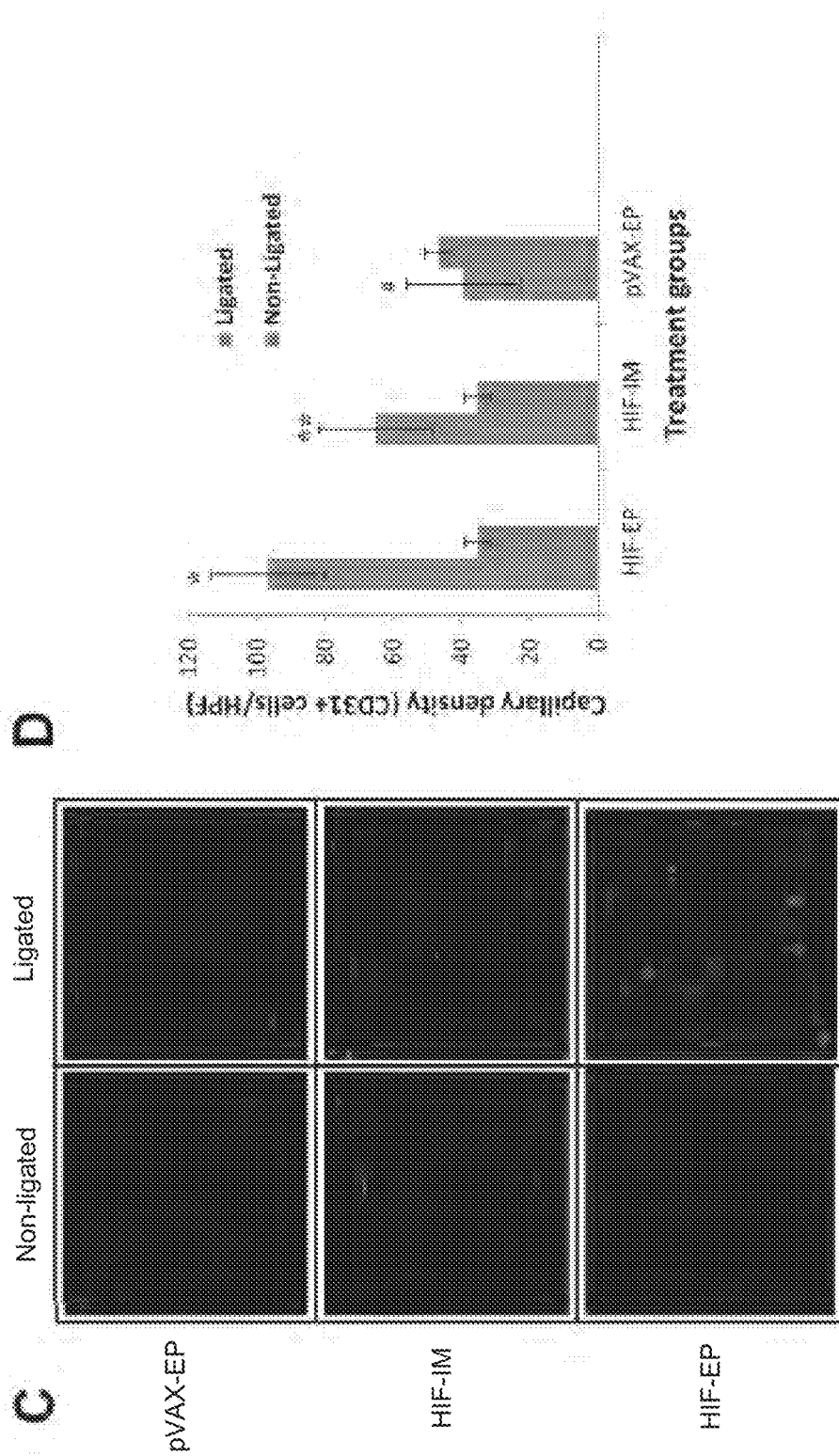
FIG. 5 (con't)

Nucleic Acid Sequence Encoding Mouse HIF-1α with Proline to Alanine Substitutions and IgE Leader Sequence

ATGGATTGGACTTGGATCTTATTTTTAGTTGCTGCTGCTACTAGAGTTCATTCTGAGG
GGGCTGGAGGGGAGAACGAAAAGAAGAAAATGTCATCTGAGAGACGAAAGGAAAA
ATCACGGGACGCCGCACGAAGTAGAAGGACAAAGGAATCTGAGGTGTTCTACGAGC
TGGCCCACCAGCTGCCTCTCCCACACAACGTGAGCTCCCATCTGGACAAGGCTTCAG
TCATGAGACTGACCATTAGCTATCTCAGGGTGAGAAAACTGCTCGATGCTGGCGGAC
TGGATAGCGAAGACGAGATGAAGGCCCAGATGGATTGCTTCTACCTGAAAGCTCTC
GACGGGTTTGTGATGGTCCTGACAGACGATGGCGACATGGTGTACATCAGTGACAA
CGTCAATAAGTATATGGGCCTGACCCAGTTTGAGCTCGCCGGACACTCCGTGTTCGA
CTTCACCCACCCTTGCGACCATGAGGAAATGCGGGAAATGCTGACTCATCGCAACG
GGCCAGTCCGAAAGGGTAAAGAGCTGAATACCCAGAGGAGCTTCTTTCTGAGAATG
AAGTGTACACTCACTAGTCGGGGCCGCACTATGAACATTAAGTCAGCCACCTGGAA
AGTGCTGCATTGCACAGGCCACATCCATGTCTACGACACCAACTCCAATCAGCCTCA
GTGTGGATATAAGAAACCCCCTATGACATGCCTGGTGCTCATTTGTGAACCCATCCC
TCACCCATCCAATATCGAGATTCCACTGGACTCTAAGACATTCCTGTCAAGACATAG
CCTCGATATGAAATTTTCCTACTGCGACGAACGGATTACTGAGCTGATGGGGTATGA
ACCCGAGGAACTGCTCGGTAGGAGCATCTACGAGTACTATCACGCCCTGGATTCCG
ACCATCTCACCAAGACACACCATGACATGTTCACAAAAGGCCAGGTGACCACAGGA
CAGTACCGGATGCTGGCTAAACGCGGGGGTTACGTGTGGGTCGAGACTCAGGCAAC
CGTGATCTACAACACTAAGAATTCTCAGCCCCAGTGCATCGTGTGCGTGAACTACGT
GGTCAGTGGAATCATTCAGCACGACCTGCTCTTTTCTCTGCAGCAGACCGAAAGTGT
GCTCAAGCCTGTCGAGTCTAGTGATATGAAGATGACCCAGCTGTTCACAAAAGTGG
AAAGTGAGGATACATCATGTCTGTTTGACAAGCTCAAGAAAGAGCCAGACGCTCTG
ACTCTGCTCGCA<u>GCT</u>GCAGCAGGCGATACCATCATTAGTCTGGACTTCGGATCAGAC
GATACTGAAACCGAGGATCAGCAGCTGGAAGACGTGCCTCTCTACAACGACGTGAT
GTTTCCATCAAGCAATGAGAAGCTGAACATCAATCTCGCCATGAGCCCCCTGCCTTC
CTCTGAAACCCCAAAACCCCTGCGGAGTTCAGCTGATCCCGCACTGAACCAGGAGG
TGGCTCTGAAGCTCGAAAGCTCCCCCGAGAGCCTGGGACTCTCCTTCACTATGCCTC
AGATCCAGGATCAGCCCGCAAGTCCTTCAGACGGGTCTACCCGCCAGTCTAGTCCTG
AACCAAACAGCCCTTCCGAGTATTGCTTCGATGTGGACAGCGATATGGTGAATGTCT
TCAAGCTGGAACTCGTCGAGAAACTGTTTGCAGAAGACACCGAGGCCAAGAACCCC
TTCAGCACACAGGACACTGATCTGGACCTGGAGATGCTGGC<u>TGCA</u>TACATTCCCATG
GACGATGACTTCCAGCTGAGGAGCTTTGATCAGCTGAGCCCCCTGGAGTCTAATAGT
CCATCACCACCCAGCATGTCCACAGTGACTGGCTTCCAGCAGACACAGCTGCAGAA
GCCAACCATCACAGCAACTGCCACTACCACAGCAACTACCGACGAATCCAAGACCG
AGACAAAGGATAACAAAGAGGACATCAAAATTCTGATCGCCTCTCCCTCAAGCACC
CAGGTGCCTCAGGAAACAACTACCGCTAAAGCATCCGCCTATTCTGGGACTCACTCT
AGAACCGCTAGTCCCGATAGAGCAGGCAAGAGAGTGATCGAGCAGACTGACAAGG
CACATCCTCGATCACTGAAACTCAGCGCCACCCTGAACCAGAGGAATACAGTGCCA
GAGGAAGAGCTGAACCCCAAGACCATTGCCTCACAGAATGCTCAGCGAAAGAGGA
AAATGGAGCACGACGGGAGCCTGTTCCAGGCAGCTGGAATCGGAACACTGCTCCAG
CAGCCAGGCGATTGTGCCCCCACTATGTCTCTGAGTTGGAAGCGCGTGAAAGGCTTT
ATTTCCTCTGAACAGAACGGAACAGAGCAGAAGACTATCATTCTGATCCCTTCCGAT

FIG. 7A

CTCGCTTGCCGACTGCTCGGGCAGTCCATGGACGAATCTGGTCTGCCACAGCTCACC
TCTTACGATTGTGAAGTGAATGCCCCCATCCAGGGTAGCCGAAATCTCCTCCAGGGT
GAAGAACTGCTCAGAGCACTCGACCAGGTGAACTGATAA (SEQ ID NO:1)

FIG. 7A (con't)

Amino Acid Sequence of Mouse HIF-1α with Proline to Alanine Substitutions and IgE Leader Sequence

<u>MDWTWILFLVAAATRVHS</u>EGAGGENEKKKMSSERRKEKSRDAARSRRTKESEVFYEL
AHQLPLPHNVSSHLDKASVMRLTISYLRVRKLLDAGGLDSEDEMKAQMDCFYLKALD
GFVMVLTDDGDMVYISDNVNKYMGLTQFELAGHSVFDFTHPCDHEEMREMLTHRNGP
VRKGKELNTQRSFFLRMKCTLTSRGRTMNIKSATWKVLHCTGHIHVYDTNSNQPQCGY
KKPPMTCLVLICEPIPHPSNIEIPLDSKTFLSRHSLDMKFSYCDERITELMGYEPEELLGRSI
YEYYHALDSDHLTKTHHDMFTKGQVTTGQYRMLAKRGGYVWVETQATVIYNTKNSQ
PQCIVCVNYVVSGIIQHDLLFSLQQTESVLKPVESSDMKMTQLFTKVESEDTSCLFDKLK
KEPDALTLLA<u>A</u>AAGDTIISLDFGSDDTETEDQQLEDVPLYNDVMFPSSNEKLNINLAMSP
LPSSETPKPLRSSADPALNQEVALKLESSPESLGLSFTMPQIQDQPASPSDGSTRQSSPEPN
SPSEYCFDVDSDMVNVFKLELVEKLFAEDTEAKNPFSTQDTDLDLEMLA<u>A</u>YIPMDDDF
QLRSFDQLSPLESNSPSPPSMSTVTGFQQTQLQKPTITATATTTATTDESKTETKDNKEDI
KILIASPSSTQVPQETTTAKASAYSGTHSRTASPDRAGKRVIEQTDKAHPRSLKLSATLNQ
RNTVPEEELNPKTIASQNAQRKRKMEHDGSLFQAAGIGTLLQQPGDCAPTMSLSWKRV
KGFISSEQNGTEQKTIILIPSDLACRLLGQSMDESGLPQLTSYDCEVNAPIQGSRNLLQGE
ELLRALDQVN (SEQ ID NO:2)

FIG. 7B

Nucleic Acid Sequence Encoding Mouse HIF-1α with Proline to Alanine Substitutions
<u>GGATCCGCCACC</u>ATGGAGGGGGCTGGAGGGGAGAACGAAAAGAAGAAAATGTCAT
CTGAGAGACGAAAGGAAAAATCACGGGACGCCGCACGAAGTAGAAGGACAAAGGA
ATCTGAGGTGTTCTACGAGCTGGCCCACCAGCTGCCTCTCCCACACAACGTGAGCTC
CCATCTGGACAAGGCTTCAGTCATGAGACTGACCATTAGCTATCTCAGGGTGAGAAA
ACTGCTCGATGCTGGCGGACTGGATAGCGAAGACGAGATGAAGGCCCAGATGGATT
GCTTCTACCTGAAAGCTCTCGACGGGTTTGTGATGGTCCTGACAGACGATGGCGACA
TGGTGTACATCAGTGACAACGTCAATAAGTATATGGGCCTGACCCAGTTTGAGCTCG
CCGGACACTCCGTGTTCGACTTCACCCACCCTTGCGACCATGAGGAAATGCGGGAA
ATGCTGACTCATCGCAACGGGCCAGTCCGAAAGGGTAAAGAGCTGAATACCCAGAG
GAGCTTCTTTCTGAGAATGAAGTGTACACTCACTAGTCGGGGCCGCACTATGAACAT
TAAGTCAGCCACCTGGAAAGTGCTGCATTGCACAGGCCACATCCATGTCTACGACAC
CAACTCCAATCAGCCTCAGTGTGGATATAAGAAACCCCTATGACATGCCTGGTGCT
CATTTGTGAACCCATCCCTCACCCATCCAATATCGAGATTCCACTGGACTCTAAGAC
ATTCCTGTCAAGACATAGCCTCGATATGAAATTTTCCTACTGCGACGAACGGATTAC
TGAGCTGATGGGGTATGAACCCGAGGAACTGCTCGGTAGGAGCATCTACGAGTACT
ATCACGCCCTGGATTCCGACCATCTCACCAAGACACACCATGACATGTTCACAAAAG
GCCAGGTGACCACAGGACAGTACCGGATGCTGGCTAAACGCGGGGGTTACGTGTGG
GTCGAGACTCAGGCAACCGTGATCTACAACACTAAGAATTCTCAGCCCCAGTGCATC
GTGTGCGTGAACTACGTGGTCAGTGGAATCATTCAGCACGACCTGCTCTTTTCTCTG
CAGCAGACCGAAAGTGTGCTCAAGCCTGTCGAGTCTAGTGATATGAAGATGACCCA
GCTGTTCACAAAAGTGGAAAGTGAGGATACATCATGTCTGTTTGACAAGCTCAAGA
AAGAGCCAGACGCTCTGACTCTGCTCGCA<u>GCT</u>GCAGCAGGCGATACCATCATTAGT
CTGGACTTCGGATCAGACGATACTGAAACCGAGGATCAGCAGCTGGAAGACGTGCC
TCTCTACAACGACGTGATGTTTCCATCAAGCAATGAGAAGCTGAACATCAATCTCGC
CATGAGCCCCCTGCCTTCCTCTGAAACCCCAAAACCCCTGCGGAGTTCAGCTGATCC
CGCACTGAACCAGGAGGTGGCTCTGAAGCTCGAAAGCTCCCCCGAGAGCCTGGGAC
TCTCCTTCACTATGCCTCAGATCCAGGATCAGCCCGCAAGTCCTTCAGACGGGTCTA
CCCGCCAGTCTAGTCCTGAACCAAACAGCCCTTCCGAGTATTGCTTCGATGTGGACA
GCGATATGGTGAATGTCTTCAAGCTGGAACTCGTCGAGAAACTGTTTGCAGAAGAC
ACCGAGGCCAAGAACCCCTTCAGCACACAGGACACTGATCTGGACCTGGAGATGCT
GGCT<u>GCA</u>TACATTCCCATGGACGATGACTTCCAGCTGAGGAGCTTTGATCAGCTGAG
CCCCCTGGAGTCTAATAGTCCATCACCACCCAGCATGTCCACAGTGACTGGCTTCCA
GCAGACACAGCTGCAGAAGCCAACCATCACAGCAACTGCCACTACCACAGCAACTA
CCGACGAATCCAAGACCGAGACAAAGGATAACAAAGAGGACATCAAAATTCTGATC
GCCTCTCCCTCAAGCACCCAGGTGCCTCAGGAAACAACTACCGCTAAAGCATCCGCC
TATTCTGGGACTCACTCTAGAACCGCTAGTCCCGATAGAGCAGGCAAGAGAGTGAT
CGAGCAGACTGACAAGGCACATCCTCGATCACTGAAACTCAGCGCCACCCTGAACC
AGAGGAATACAGTGCCAGAGGAAGAGCTGAACCCCAAGACCATTGCCTCACAGAAT
GCTCAGCGAAAGAGGAAAATGGAGCACGACGGGAGCCTGTTCCAGGCAGCTGGAAT
CGGAACACTGCTCCAGCAGCCAGGCGATTGTGCCCCACTATGTCTCTGAGTTGGAA
GCGCGTGAAAGGCTTTATTTCCTCTGAACAGAACGGAACAGAGCAGAAGACTATCA
TTCTGATCCCTTCCGATCTCGCTTGCCGACTGCTCGGGCAGTCCATGGACGAATCTG
GTCTGCCACAGCTCACCTCTTACGATTGTGAAGTGAATGCCCCATCCAGGGTAGCC
GAAATCTCCTCCAGGGTGAAGAACTGCTCAGAGCACTCGACCAGGTGAAC<u>TGATAA
CTCGAG</u> (SEQ ID NO:3)

FIG. 8A

Amino Acid Sequence of Mouse HIF-1α with Proline to Alanine Substitutions
MEGAGGENEKKKMSSERRKEKSRDAARSRRTKESEVFYELAHQLPLPHNVSSHLDKAS
VMRLTISYLRVRKLLDAGGLDSEDEMKAQMDCFYLKALDGFVMVLTDDGDMVYISDN
VNKYMGLTQFELAGHSVFDFTHPCDHEEMREMLTHRNGPVRKGKELNTQRSFFLRMK
CTLTSRGRTMNIKSATWKVLHCTGHIHVYDTNSNQPQCGYKKPPMTCLVLICEPIPHPSN
IEIPLDSKTFLSRHSLDMKFSYCDERITELMGYEPEELLGRSIYEYYHALDSDHLTKTHHD
MFTKGQVTTGQYRMLAKRGGYVWVETQATVIYNTKNSQPQCIVCVNYVVSGIIQHDLL
FSLQQTESVLKPVESSDMKMTQLFTKVESEDTSCLFDKLKKEPDALTLLA<u>A</u>AAGDTIISL
DFGSDDTETEDQQLEDVPLYNDVMFPSSNEKLNINLAMSPLPSSETPKPLRSSADPALNQ
EVALKLESSPESLGLSFTMPQIQDQPASPSDGSTRQSSPEPNSPSEYCFDVDSDMVNVFKL
ELVEKLFAEDTEAKNPFSTQDTDLDLEMLA<u>A</u>YIPMDDDFQLRSFDQLSPLESNSPSPPSM
STVTGFQQTQLQKPTITATATTTATTDESKTETKDNKEDIKILIASPSSTQVPQETTTAKAS
AYSGTHSRTASPDRAGKRVIEQTDKAHPRSLKLSATLNQRNTVPEEELNPKTIASQNAQ
RKRKMEHDGSLFQAAGIGTLLQQPGDCAPTMSLSWKRVKGFISSEQNGTEQKTIILIPSD
LACRLLGQSMDESGLPQLTSYDCEVNAPIQGSRNLLQGEELLRALDQVN (SEQ ID NO:4)

FIG. 8B

Nucleic Acid Sequence Encoding Human HIF-1α with Proline to Alanine Substitutions
ATGGAGGGCGCCGGCGGCGCGAACGACAAGAAAAAGATAAGTTCTGAACGTCGAA
AAGAAAAGTCTCGAGATGCAGCCAGATCTCGGCGAAGTAAAGAATCTGAAGTTTTT
TATGAGCTTGCTCATCAGTTGCCACTTCCACATAATGTGAGTTCGCATCTTGATAAG
GCCTCTGTGATGAGGCTTACCATCAGCTATTTGCGTGTGAGGAAACTTCTGGATGCT
GGTGATTTGGATATTGAAGATGACATGAAAGCACAGATGAATTGCTTTTATTTGAAA
GCCTTGGATGGTTTTGTTATGGTTCTCACAGATGATGGTGACATGATTTACATTTCTG
ATAATGTGAACAAATACATGGGATTAACTCAGTTTGAACTAACTGGACACAGTGTGT
TTGATTTTACTCATCCATGTGACCATGAGGAAATGAGAGAAATGCTTACACACAGAA
ATGGCCTTGTGAAAAAGGGTAAAGAACAAAACACACAGCGAAGCTTTTTTCTCAGA
ATGAAGTGTACCCTAACTAGCCGAGGAAGAACTATGAACATAAAGTCTGCAACATG
GAAGGTATTGCACTGCACAGGCCACATTCACGTATATGATACCAACAGTAACCAAC
CTCAGTGTGGGTATAAGAAACCACCTATGACCTGCTTGGTGCTGATTTGTGAACCCA
TTCCTCACCCATCAAATATTGAAATTCCTTTAGATAGCAAGACTTTCCTCAGTCGACA
CAGCCTGGATATGAAATTTCTTATTGTGATGAAAGAATTACCGAATTGATGGGATA
TGAGCCAGAAGAACTTTTAGGCCGCTCAATTTATGAATATTATCATGCTTTGGACTC
TGATCATCTGACCAAAACTCATCATGATATGTTTACTAAAGGACAAGTCACCACAGG
ACAGTACAGGATGCTTGCCAAAAGAGGTGGATATGTCTGGGTTGAAACTCAAGCAA
CTGTCATATATAACACCAAGAATTCTCAACCACAGTGCATTGTATGTGTGAATTACG
TTGTGAGTGGTATTATTCAGCACGACTTGATTTTCTCCCTTCAACAAACAGAATGTGT
CCTTAAACCGGTTGAATCTTCAGATATGAAAATGACTCAGCTATTCACCAAAGTTGA
ATCAGAAGATACAAGTAGCCTCTTTGACAAACTTAAGAAGGAACCTGATGCTTTAAC
TTTGCTGGCC<u>GC</u>AGCCGCTGGAGACACAATCATATCTTTAGATTTTGGCAGCAACGA
CACAGAAACTGATGACCAGCAACTTGAGGAAGTACCATTATATAATGATGTAATGC

FIG. 9A

TCCCCTCACCCAACGAAAAATTACAGAATATAAATTTGGCAATGTCTCCATTACCCA
CCGCTGAAACGCCAAAGCCACTTCGAAGTAGTGCTGACCCTGCACTCAATCAAGAA
GTTGCATTAAAATTAGAACCAAATCCAGAGTCACTGGAACTTTCTTTTACCATGCCC
CAGATTCAGGATCAGACACCTAGTCCTTCCGATGGAAGCACTAGACAAAGTTCACCT
GAGCCTAATAGTCCCAGTGAATATTGTTTTATGTGGATAGTGATATGGTCAATGAA
TTCAAGTTGGAATTGGTAGAAAACTTTTGCTGAAGACACAGAAGCAAAGAACCC
ATTTTCTACTCAGGACACAGATTTAGACTTGGAGATGTTAGCT<u>GCT</u>TATATCCCAAT
GGATGATGACTTCCAGTTACGTTCCTTCGATCAGTTGTCACCATTAGAAAGCAGTTC
CGCAAGCCCTGAAAGCGCAAGTCCTCAAAGCACAGTTACAGTATTCCAGCAGACTC
AAATACAAGAACCTACTGCTAATGCCACCACTACCACTGCCACCACTGATGAATTAA
AAACAGTGACAAAAGACCGTATGGAAGACATTAAAATATTGATTGCATCTCCATCTC
CTACCCACATACATAAAGAAACTACTAGTGCCACATCATCACCATATAGAGATACTC
AAAGTCGGACAGCCTCACCAAACAGAGCAGGAAAAGGAGTCATAGAACAGACAGA
AAAATCTCATCCAAGAAGCCCTAACGTGTTATCTGTCGCTTTGAGTCAAAGAACTAC
AGTTCCTGAGGAAGAACTAAATCCAAAGATACTAGCTTTGCAGAATGCTCAGAGAA
AGCGAAAAATGGAACATGATGGTTCACTTTTTCAAGCAGTAGGAATTGGAACATTAT
TACAGCAGCCAGACGATCATGCAGCTACTACATCACTTTCTTGGAAACGTGTAAAAG
GATGCAAATCTAGTGAACAGAATGGAATGGAGCAAAAGACAATTATTTTAATACCC
TCTGATTTAGCATGTAGACTGCTGGGGCAATCAATGGATGAAAGTGGATTACCACAG
CTGACCAGTTATGATTGTGAAGTTAATGCTCCTATACAAGGCAGCAGAAACCTACTG
CAGGGTGAAGAATTACTCAGAGCTTTGGATCAAGTTAACTGA (SEQ ID NO:5)

FIG 9A (con't)

Amino Acid Sequence of Human HIF-1α with Proline to Alanine Substitutions
MEGAGGANDKKKISSERRKEKSRDAARSRRSKESEVFYELAHQLPLPHNVSSHLDKASV
MRLTISYLRVRKLLDAGDLDIEDDMKAQMNCFYLKALDGFVMVLTDDGDMIYISDNV
NKYMGLTQFELTGHSVFDFTHPCDHEEMREMLTHRNGLVKKGKEQNTQRSFFLRMKC
TLTSRGRTMNIKSATWKVLHCTGHIHVYDTNSNQPQCGYKKPPMTCLVLICEPIPHPSNI
EIPLDSKTFLSRHSLDMKFSYCDERITELMGYEPEELLGRSIYEYYHALDSDHLTKTHHD
MFTKGQVTTGQYRMLAKRGGYVWVETQATVIYNTKNSQPQCIVCVNYVVSGIIQHDLI
FSLQQTECVLKPVESSDMKMTQLFTKVESEDTSSLFDKLKKEPDALTLLA<u>A</u>AAGDTIISL
DFGSNDTETDDQQLEEVPLYNDVMLSPPNEKLQNINLAMSPLPTAETPKPLRSSADPAL
NQEVALKLEPNPESLELSFTMPQIQDQTPSPDGSTRQSSPEPNSPSEYCFYVDSDMVNEF
KLELVEKLFAEDTEAKNPFSTQDTDLDLEMLA<u>A</u>YIPMDDDFQLRSFDQLSPLESSSASPE
SASPQSTVTVFQQTQIQEPTANATTTTATTDELKTVTKDRMEDIKILIASPSPTHIHKETTS
ATSSPYRDTQSRTASPNRAGKGVIEQTEKSHPRSPNVLSVALSQRTTVPEEELNPKILALQ
NAQRKRKMEHDGSLFQAVGIGTLLQQPDDHAATTSLSWKRVKGCKSSEQNGMEQKTII
LIPSDLACRLLGQSMDESGLPQLTSYDCEVNAPIQGSRNLLQGEELLRALDQVN (SEQ ID
NO:6)

FIG. 9B

COMPOSITIONS COMPRISING HYPOXIA INDUCIBLE FACTOR-1 ALPHA AND METHODS OF USING THE SAME

CROSS-REFERENCE TO RELATED APPLICATIONS

This application is the U.S. national stage application filed under 35 U.S.C. § 371 claiming benefit to International Patent Application No. PCT/US14/29263, filed Mar. 14, 2014, which is entitled to priority under 35 U.S.C. § 119(e) to U.S. Provisional Application No. 61/800,703, filed Mar. 15, 2013, each of which is hereby incorporated by reference in its entirety.

STATEMENT OF GOVERNMENT INTEREST

This invention was made with government support under contract number K12 HL083772-01 awarded by the National Institutes of Health. The government has certain rights in the invention.

TECHNICAL FIELD

The present invention relates to compositions comprising hypoxia inducible factor-1 alpha (HIF-1α) and methods of treating hypoxia or ischemia.

BACKGROUND

In mammals, embryo development and maintenance of adult homeostatsis depend on the establishment of a functional vascular system that supplies oxygen ($O_2$) and other nutrients to the tissues and cells of the mammal Local oxygen delivery to these tissues and cells is regulated by the circulatory system through transient changes in the tone of pre-existing blood vessels, the establishment of new blood vessels (angiogenesis), and the remodeling of existing blood vessels to accept increased blood flow (arteriogenesis). Tissue perfusion under physiological and pathological conditions is regulated by hypoxia inducible factor-1 (HIF-1).

HIF-1 is a heterodimeric transcription factor composed of an oxygen-regulated alpha subunit (HIF-1α) and a constitutively expressed beta subunit (HIF-1β). HIF-1 mediates adaptive responses to hypoxia and ischemia in nucleated cells of metazoan organisms by directing transcription of genes involved in vascular homeostasis through effects on vascular tone, angiogenesis, and/or arteriogenesis. In pathological conditions, such as critical limb ischemia (CLI), HIF-1 can be inhibited, leading to decreased tissue perfusion, manifestation of ischemic pain at rest, ulceration, and/or gangrene, and eventually limb amputation.

Accordingly, a need exists for the identification and development of compositions and methods for treating disease associated with ischemia and/or hypoxia, including increasing tissue perfusion of the affected tissues and restoring normal physiological responses to ischemia and hypoxia.

SUMMARY

The present invention is directed to a therapeutic comprising hypoxia inducible factor-1 alpha (HIF-1 α). The present invention is also directed to a method of treating hypoxia or ischemia in a subject in need thereof. The method can comprise administering the therapeutic to the subject.

BRIEF DESCRIPTION OF THE DRAWINGS

FIG. 7 shows (A) a nucleic acid sequence encoding mouse HIF-1α, in which underlining indicates the start codon and nucleotides encoding the IgE leader sequence and double underlining and bold indicates the codons encoding alanine in lieu of proline; and (B) the amino acid sequence of mouse HIF-1α, in which underlining indicates the initiator methionine and IgE leader sequence linked to the HIF-1α amino acid sequence and double underlining and bold indicates the alanine residues that have been substituted for the wild-type proline residues in the amino acid sequence of HIF-1α.

FIG. 8 shows (A) a nucleic acid sequence encoding mouse HIF-1α, in which underlining at the 5' end indicates the BamHI restriction site (i.e., GGA TCC) for cloning purposes and Kozak sequence (i.e., GCC ACC), underlining at the 3' end indicates the stop codons (i.e., TGA TAA) and the XhoI restriction site (i.e., CTC GAG) for cloning purposes, and double underlining and bold indicates the codons encoding alanine in lieu of proline; and (B) the amino acid sequence of mouse HIF-1α, in which double underlining and bold indicates the alanine residues that have been substituted for the wild-type proline residues in the amino acid sequence of HIF-1α.

FIG. 9 shows (A) a nucleic acid sequence encoding human HIF-1α, in which double underlining and bold indicates the codons encoding alanine in lieu of proline; and (B) the amino acid sequence of human HIF-1α, in which double underlining and bold indicates the alanine residues that have been substituted for the wild-type proline residues in the amino acid sequence of HIF-1α.

DETAILED DESCRIPTION

Figure 1:
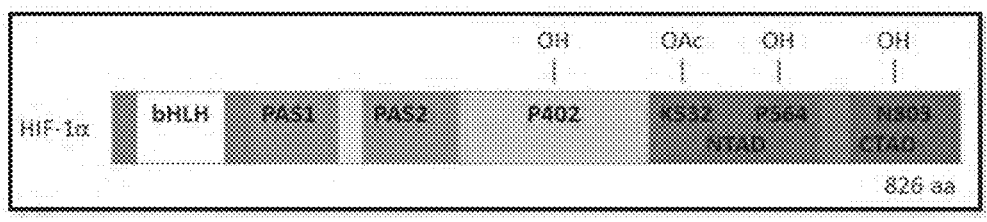
FIG. 1 shows a schematic, illustrating features of hypoxia inducible factor-1 alpha (HIF-1α) protein.

The present invention relates to a therapeutic for treating hypoxia or ischemia. The therapeutic can comprise hypoxia inducible factor-1 alpha (HIF-1α). The therapeutic can promote or induce vascularization. The therapeutic can increase capillary density, collateral vessel formation, vessel size, or a combination thereof in the subject administered the therapeutic as compared to a subject not administered the therapeutic. The therapeutic can increase tissue perfusion in the subject administered the therapeutic as compared to the subject not administered the therapeutic. The therapeutic can decrease tissue necrosis in the subject administered the therapeutic as compared to the subject not administered the therapeutic.

Accordingly, the therapeutic can be used in a method of treating hypoxia or ischemia. The hypoxia or ischemia can be associated with critical limb ischemia.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein means a nucleic acid sequence or a portion thereof that encodes a polypeptide capable of capable of altering or affecting a change in vascular homeostasis in a mammal, for example, but not limited to, through effects on vascular tone, angiogenesis, and/or arteriogenesis. The fragments can be DNA fragments selected from at least one of the various nucleotide sequences that encode protein fragments set forth below. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" with respect to polypeptide sequences means a polypeptide capable of altering or affecting a change in vascular homeostasis in a mammal, for example, but not limited to, through effects on vascular tone, angiogenesis, and/or arteriogenesis. The fragments can be polypeptide fragments selected from at least one of the various amino acid sequences set forth below. Fragments can comprise at least 10%, at least 20%, at least 30%, at least 40%, at least 50%, at least 60%, at least 70%, at least 80%, at least 90%, or at least 95% of one or more of the proteins set forth below. In some embodiments, fragments can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, at least 240 amino acids or more of at least one of the proteins set forth below.

"Genetic construct" or "construct" as used herein refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs or constructs that contain the necessary regulatory elements operably linked to a coding sequence that encodes a protein such that when present in the cell of the individual, the coding sequence will be expressed.

"Hypoxia" as used herein means a reduction in ambient oxygen ($O_2$) concentration.

"Identical" or "identity" as used herein in the context of two or more nucleic acid or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Ischemia" as used herein means a condition in which tissue perfusion is reduced such that oxygen ($O_2$) availability is insufficient to meet tissue metabolic requirements.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein or amino acid sequence set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described therapeutics. The can be a human, chimpanzee, dog, cat, horse, cow, mouse, or rat.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of an animal from a disease through means of preventing, suppressing, repressing, or completely eliminating the disease. Preventing the disease involves administering a therapeutic of the present invention to an animal prior to onset of the disease. Suppressing the disease involves administering a therapeutic of the present invention to an animal after induction of the disease but before its clinical appearance. Repressing the disease involves administering a therapeutic of the present invention to an animal after clinical appearance of the disease. The disease may be associated with hypoxia and/or ischemia.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof A variant may be an amino acid sequence that is substantially identical over the full length of the amino acid sequence or fragment thereof The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Therapeutic

The therapeutic can comprise an agent, a fragment thereof, a variant thereof, or a combination thereof The agent can promote or induce vascularization. The agent can promote or induce vascular tone, angiogenesis, and/or arteriogenesis. The therapeutic can increase capillary density, collateral vessel formation, vessel size, or a combination thereof in the subject administered the therapeutic as compared to a subject not administered the therapeutic. The therapeutic can increase tissue perfusion in the subject administered the therapeutic as compared to the subject not administered the therapeutic. The therapeutic can decrease tissue necrosis in the subject administered the therapeutic as compared to the subject not administered the therapeutic.

The therapeutic of the present invention can have features required of effective therapeutics such as being safe so the therapeutic itself does not cause illness or death; protective against illness; and provides a ease of administration, few side effects, biological stability, and low cost per dose. The therapeutic can accomplish some or all of these features by inclusion of the agent.

a. Agent

The therapeutic can comprise the agent. The agent can be a nucleic acid sequence, an amino acid sequence, or a combination thereof The nucleic acid sequence can be DNA, RNA, cDNA, a variant thereof, a fragment thereof, or a combination thereof The nucleic acid sequence can also include additional sequences that encode linker or tag sequences that are linked to the agent by a peptide bond. The amino acid sequence can be a protein, a peptide, a variant thereof, a fragment thereof, or a combination thereof.

(1) HIF-1α

The agent can be hypoxia inducible factor-1 alpha (HIF-1α), a fragment thereof, a variant thereof, or a combination thereof HIF-1α is one of two subunits of the transcription factor HIF-1. The other subunit is HIF-1β. Accordingly, HIF-1 is a heterodimer of the alpha and beta subunits, in which the beta subunit is constitutively expressed and stability of the alpha subunit is regulated by oxygen concentration.

Both subunits are members of the basic Helix-Loop-Helix PER-ARNT-SIM (bHLH-PAS) family of transcription factors. As shown in FIG. 1, HIF-1α contains a bHLH domain and two PAS domains as well as an N-terminal transactivation domain (NTAD) and a C-terminal transactivation domain (CTAD). Additionally, HIF-1α contains two proline residues (e.g., P402 and P564 in human HIF-1α) that are hydroxylated by enzymes containing a prolyl-hydroxylase domain (PHD), namely, PHD 1, PHD2, and PHD3, and an asparagine residue located in the CTAD (e.g., N803 in human HIF-1α) that is hydroxylated via factor inhibiting HIF (FIH). These residues are hydroxylated in HIF-la in the presence of oxygen.

Specifically, the hydroxylated asparagine residue sterically inhibits interactions between HIF-1α and transcriptional coactivators while the hydroxylated proline residues are recognized and bound by von Hippel-Lindau tumor suppressor protein (pVHL). pVHL is found in a complex including elongin B, elongin C, and cullin-2 and possesses ubiquitin ligase E3 activity. This complex mediates ubiquitination of hydroxylated HIF-1α, which is followed by degradation via the 26S proteasome.

Accordingly, in the presence of normoxia, HIF-1α is labile and/or unable to interact with transcriptional coactivators, and thus, HIF-1 is inactive. Under hypoxic or ischemic conditions, hydroxylation of HIF-1α is reduced or inhibited, thereby stabilizing HIF-1α and allowing HIF-1 to mediate adaptive responses to hypoxia and ischemia. These adaptive responses can include directing transcription of genes involved in vascular homeostasis through effects on vascular tone, angiogenesis, and/or arteriogenesis.

Under pathological conditions, however, HIF-1 can be inhibited, leading to decreased tissue perfusion, manifestation of ischemic pain at rest, ulceration, and/or gangrene, and eventually amputation. Such pathological conditions may include critical limb ischemia.

Accordingly, the therapeutic can be used for treating pathological conditions involving hypoxia and/or ischemia. The hypoxia or ischemia can be associated with critical limb ischemia, peripheral artery disease, wound healing, a vascular disease, a circulatory disease, coronary artery disease, cardiovascular disease, diabetes, or a combination thereof. The hypoxia or ischemia can be associated with critical limb ischemia.

The therapeutic can increase capillary density, collateral vessel formation, vessel size, or a combination thereof in the subject administered the therapeutic as compared to a subject not administered the therapeutic. The therapeutic can increase tissue perfusion in the subject administered the therapeutic as compared to the subject not administered the therapeutic. The therapeutic can decrease tissue necrosis in the subject administered the therapeutic as compared to the subject not administered the therapeutic.

A nucleic acid encoding HIF-1α can be from any number of organisms, for example, mouse (*Mus musculus*) and human (*Homo sapiens*). The nucleic acid encoding HIF-1α can be optimized with regards to codon usage and corresponding RNA transcripts. The nucleic acid encoding HIF-1α can be codon and RNA optimized for expression. In some embodiments, the nucleic acid encoding HIF-la can include a Kozak sequence (e.g., GCC ACC) to increase the efficiency of translation. The nucleic acid encoding HIF-1α can include multiple stop codons (e.g., TGA TGA, TGA TAA, and so forth) to increase the efficiency of translation termination. The nucleic acid encoding HIF-1α can also encode an immunoglobulin E (IgE) leader sequence. The IgE leader sequence can be located 5' to the HIF-1α in the nucleic acid. The nucleic acid encoding HIF-1α can also include a nucleotide sequence encoding the IgE leader sequence. In some embodiments, the nucleic acid encoding HIF-1α is free of or does not contain a nucleotide sequence encoding the IgE leader sequence.

In some embodiments, the nucleic acid encoding HIF-1α can be a heterologous nucleic acid sequence and/or contain or include one or more heterologous nucleic acid sequences. The nucleic acid encoding HIF-1α can be mutated such that one or more amino acids or residues in an amino acid sequence of HIF-1α is replaced or substituted with another amino acid or residue. The nucleic acid encoding HIF-1α can be mutated such that one or more residues in the amino acid sequence of HIF-1α that can be hydroxylated (e.g., proline, asparagine, etc.) are replaced or substituted with a residue that cannot be hydroxylated. The nucleic acid encoding HIF-1α can be mutated such that one or more proline residues in the amino acid sequence of HIF-1α are replaced or substituted with a residue that cannot be hydroxylated. The nucleic acid encoding HIF-1α can be mutated such that the amino acid sequence of HIF-1α cannot be recognized and/or bound by pVHL. The nucleic acid encoding HIF-1α can be mutated such that the amino acid sequence of HIF-1α cannot be ubiquinated. The nucleic acid encoding HIF-1α can be mutated such that the amino acid sequence of HIF-1α cannot be degraded, for example, but not limited to, the 26S proteasome. The nucleic acid encoding HIF-1α can be mutated such that the amino acid sequence of HIF-1α is stabile regardless of the oxygen concentration in a cell and/or tissue, and thus, HIF-1α protein may accumulate in the cell and/or tissue.

The mouse HIF-1α can be the nucleic acid sequence SEQ ID NO:1, which encodes for SEQ ID NO:2 (FIGS. 7A and 7B). SEQ ID NO:2 is an amino acid sequence of mouse HIF-1α, in which two proline residues have been replaced with an alanine. This replacement can prevent or reduce hydroxylation of HIF-1α and thus recognition of HIF-1α by pVHL. SEQ ID NO:2 is the amino acid sequence of mouse HIF-1α linked via a peptide bond to an IgE leader sequence.

In some embodiments, the mouse HIF-1α can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:1. In other embodiments, the mouse HIF-1α can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. The mouse HIF-1α can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

In some embodiments, the mouse HIF-1α can be the nucleic acid sequence SEQ ID NO:3, which encodes for SEQ ID NO:4 (FIGS. 8A and 8B). SEQ ID NO:4 is an amino acid sequence of mouse HIF-1α, in which two proline residues have been replaced with an alanine as shown in FIG. 8B. This replacement can prevent or reduce hydroxylation of HIF-1α and thus recognition of HIF-1α by pVHL.

SEQ ID NO:4 is the amino acid sequence of mouse HIF-1α that is not linked via a peptide bond to an IgE leader sequence.

In some embodiments, the mouse HIF-1α can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:3. In other embodiments, the mouse HIF-1α can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4. The mouse HIF-1α can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4.

The human HIF-1α can be the nucleic acid sequence SEQ ID NO:5, which encodes for SEQ ID NO:6 (FIGS. 9A and 9B). SEQ ID NO:6 is an amino acid sequence of human HIF-1α, in which two proline residues have been replaced with an alanine as shown in FIG. 9B. This replacement can prevent or reduce hydroxylation of HIF-1α and thus recognition of HIF-1α by pVHL.

In some embodiments, the human HIF-1α can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:5. In other embodiments, the human HIF-1α can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. The human HIF-1α can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6.

Some embodiments relate to fragments of SEQ ID NO:1, SEQ ID NO:3, and SEQ ID NO:5. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:1, SEQ ID NO:3, and/or SEQ ID NO:5. In some embodiments, fragments can include sequences that encode a leader sequence, for example, an immunoglobulin leader sequence, such as the IgE leader sequence. In some embodiments, fragments can be free of coding sequences that encode a leader sequence.

Fragments of nucleic acids with nucleotide sequences having identity to fragments of SEQ ID NO:1, SEQ ID NO:3, and/or SEQ ID NO:5 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:1, SEQ ID NO:3, and/or SEQ ID NO:5. Some embodiments relate to fragments that have 96% or greater identity to the fragments of HIF-1α nucleic acid sequences herein. Some embodiments relate to fragments that have 97% or greater identity to the fragments of HIF-1α nucleic acid sequences herein. Some embodiments relate to fragments that have 98% or greater identity to the fragments of HIF-1α nucleic acid sequences herein. Some embodiments relate to fragments that have 99% or greater identity to the fragments of HIF-1α nucleic acid sequences herein. In some embodiments, fragments can include sequences that encode a leader sequence, for example, an immunoglobulin leader sequence, such as the IgE leader sequence. In some embodiments, fragments can be free of coding sequences that encode a leader sequence.

Fragments of SEQ ID NO:2, SEQ ID NO:4, and SEQ ID NO:6 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2, SEQ ID NO:4, and/or SEQ ID NO:6. In some embodiments, fragments include a leader sequence, for example, an immunoglobulin leader sequence, such as the IgE leader sequence. In other embodiments, fragments can be free of a leader sequence.

Fragments of proteins with amino acid sequences having identity to fragments of SEQ ID NO:2, SEQ ID NO:4, and/or SEQ ID NO:6 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:2, SEQ ID NO:4, and/or SEQ ID NO:6. Some embodiments relate fragments having 96% or greater identity to the fragments of HIF-1α protein sequences herein. Some embodiments relate to fragments having 97% or greater identity to the fragments of HIF-1α protein sequences herein. Some embodiments relate to fragments having 98% or greater identity to the fragments of HIF-1α protein sequences herein. Some embodiments relate to fragments having 99% or greater identity to the fragments of HIF-1α protein sequences herein. In some embodiments, fragments include a leader sequence, for example, an immunoglobulin leader sequence, such as the IgE leader sequence. In other embodiments, fragments can be free of a leader sequence.

b. Vector

The therapeutic can comprise one or more vectors that include a heterologous nucleic acid encoding the agent. The one or more vectors can be capable of expressing the agent. The vector may comprise heterologous nucleic acid encoding the agent. The vector can have a nucleic acid sequence containing an origin of replication. The vector can be a plasmid, bacteriophage, bacterial artificial chromosome, or yeast artificial chromosome. The vector can be either a self-replicating extra chromosomal vector or a vector that integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the agent-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing DNA encoding the antigen, or the adjuvant and enabling a cell to translate the sequence to an antigen that is recognized by the immune system, or the adjuvant.

Also provided herein is a linear nucleic acid, or linear expression cassette ("LEC"), that is capable of being efficiently delivered to a subject via electroporation and expressing the desired agent(s). The LEC may be any linear DNA devoid of any phosphate backbone. The DNA may encode the agent(s). The LEC may contain a promoter, an intron, a stop codon, and/or a polyadenylation signal. The expression of the agent may be controlled by the promoter. The LEC may not contain any antibiotic resistance genes and/or a phosphate backbone. The LEC may not contain other nucleic acid sequences unrelated to the desired agent gene expression.

The LEC may be derived from any plasmid capable of being linearized. The plasmid may be capable of expressing the agent(s). The plasmid can be pNP (Puerto Rico/34) or pM2 (New Caledonia/99). The plasmid may be WLV009, pVAX, pcDNA3.0, or provax, or any other expression vector capable of expressing DNA encoding the agent, enabling a cell to translate the sequence to the agent.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the agent sequence(s) described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the agent and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

c. Excipients and other Components of the Therapeutic

The therapeutic may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate is may be present in the therapeutic at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid therapeutics may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the therapeutic is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The therapeutic may further comprise a genetic facilitator agent as described in U.S. Ser. No. 021,579 filed Apr. 1, 1994, which is fully incorporated by reference.

The therapeutic can be formulated according to the mode of administration to be used. An injectable therapeutic pharmaceutical composition can be sterile, pyrogen free and particulate free. An isotonic formulation or solution can be used. Additives for isotonicity can include sodium chloride, dextrose, mannitol, sorbitol, and lactose. The therapeutic can comprise a vasoconstriction agent. The isotonic solutions can include phosphate buffered saline. Therapeutic can further comprise stabilizers including gelatin and albumin. The stabilizers can allow the formulation to be stable at room or ambient temperature for extended periods of time, including LGS or polycations or polyanions.

3. Method of Treatment

The present invention is also directed to a method of treating hypoxia or ischemia in a subject in need thereof The method can include administering the herein disclosed therapeutic to the subject. The subject administered the therapeutic can have increased capillary density, collateral vessel formation, vessel size, or a combination thereof The subject administered the therapeutic can have increased tissue perfusion. The subject administered the therapeutic can have decreased tissue necrosis.

The hypoxia or ischemia can be associated with critical limb ischemia, peripheral artery disease, wound healing, a vascular disease, a circulatory disease, coronary artery disease, cardiovascular disease, diabetes, or a combination thereof The hypoxia or ischemia can be associated with critical limb ischemia. The method of treatment can reduce, eliminate, or prevent critical limb ischemia in the subject in need thereof The therapeutic dose can be between 1 µg to 10 mg active component/kg body weight/time, and can be 20 µg to 10 mg component/kg body weight/time. The therapeutic can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of therapeutic doses for effective treatment can be 1, 2, 3, 4, 5, 6, 7, 8, 9, 10, or more doses.

a. Administration

The therapeutic can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The therapeutic can be administered prophylactically or therapeutically. In prophylactic administration, the therapeutics can be administered in an amount sufficient to induce an immune response. In therapeutic applications, the therapeutics are administered to a subject in need thereof in an amount sufficient to elicit a therapeutic effect. An amount adequate to accomplish this is defined as "therapeutically effective dose." Amounts effective for this use will depend on, e.g., the particular composition of the therapeutic regimen administered, the manner of administration, the stage and severity of the disease, the general state of health of the patient, and the judgment of the prescribing physician.

The therapeutic can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the therapeutic can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The therapeutics can be delivered via a variety of routes. Typical delivery routes include parenteral administration, e.g., intradermal, intramuscular or subcutaneous delivery. Other routes include oral administration, intranasal, and intravaginal routes. For the DNA of the therapeutic in particular, the therapeutic can be delivered to the interstitial spaces of tissues of an individual (Felgner et al., U.S. Pat. Nos. 5,580,859 and 5,703,055, the contents of all of which are incorporated herein by reference in their entirety). The therapeutic can also be administered to muscle, or can be administered via intradermal or subcutaneous injections, or transdermally, such as by iontophoresis. Epidermal administration of the therapeutic can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The therapeutic can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the therapeutic.

The therapeutic can be a liquid preparation such as a suspension, syrup or elixir. The therapeutic can also be a preparation for parenteral, subcutaneous, intradermal, intramuscular or intravenous administration (e.g., injectable administration), such as a sterile suspension or emulsion.

The therapeutic can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The therapeutic can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241, 701; 6,233,482; 6,216,034; 6,208,893; 6,192,270; 6,181, 964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the therapeutic described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the therapeutic into tissue without the use of a needle. The MID may inject the therapeutic as a small stream or jet with such force that the therapeutic pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired therapeutic in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the therapeutic into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver therapeutics to all types of tissues, particularly to skin and mucosa. In some embodiments, a needle-free injector may be used to propel a liquid that contains the therapeutic to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle injectors that deliver the therapeutic and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described therapeutic herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

4. Examples

Example 1

Materials and Methods for Examples 2-5

The experiments described below in Examples 2-5 used the methods described herein in Example 1 and investigated the stimulation of angiogenesis during tissue ischemia. In particular, the investigation examined the stimulation of angiogenesis by HIF-1α during tissue ischemia. A DNA plasmid encoding constitutively expressed HIF-1α gene (as described above and thus including the proline to alanine substitutions) was administered by in vivo electroporation (EP) or intramuscular (IM) injection alone.

Summary of Method

Left femoral artery ligation was performed in mice assigned to three groups: (1) HIF-EP (n=13); (2) HIF-IM (n=14); and (3) empty plasmid (pVAX)-EP (n=12). A single dose of HIF-1α or pVAX DNA (20 μL of 5 μg/μL each) was injected into the ischemic adductor muscle followed by EP (groups one and three). Mice in group two received IM injection of HIF-la plasmid DNA alone. From preligation to days 0, 3, 7, 14, and 21 postligation, limb perfusion recovery quantified by laser Doppler perfusion imager, limb function, and limb necrosis were measured as described below in more detail. On day 21, the surviving mice (4-5 per group) were sacrificed and adductor muscle tissues were stained for necrosis using hematoxylin and eosin, capillary density (anti-CD31 antibodies), and collateral vessels via anti-a-smooth muscle actin antibodies as described below in more detail.

Detailed Method

Figure 2:
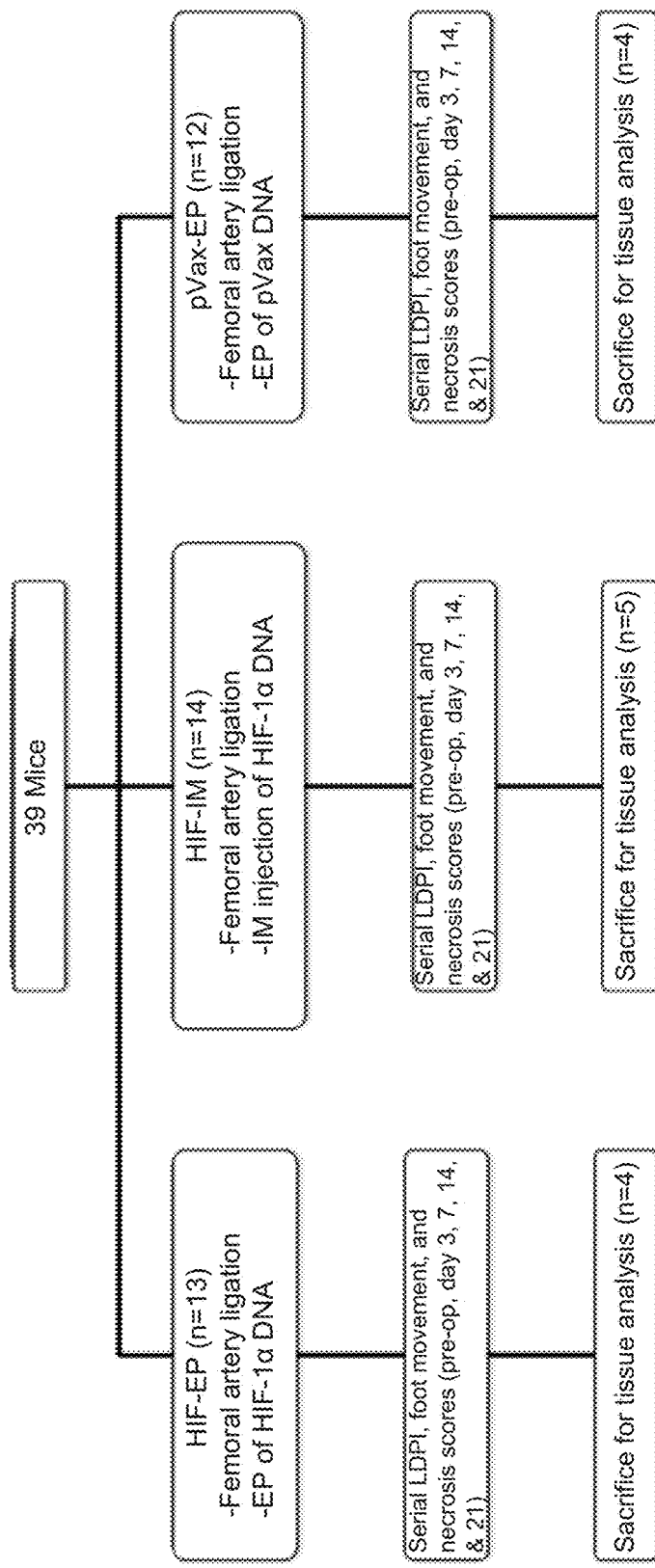
FIG. 2 shows a schematic illustrating a summary of experimental study design. EP, Electroporation; HIF-1a, hypoxia-inducible factor 1 alpha; IM, intramuscular injection; LDPI, laser Doppler perfusion imager; pVAX, empty backbone plasmid DNA.

Experimental Protocol. Experiments were performed (FIG. 2) to assess the following variables: (1) evaluate recovery of limb perfusion over time using ultrasound laser Doppler; (2) investigate the extent of limb salvage and survival from autoamputation; and (3) assess improvement in tissue histological features including degree of tissue necrosis. Thirty-nine age- and gender-matched wild-type Balb/c mice were assigned into one of the following three treatment groups: (1) 13 mice (active treatment, HIF-1a DNA/EP); (2) 14 mice (positive control, HIF-1a DNA/IM); and (3) 12 mice (negative control, empty plasmid [pVAX] DNA/EP). The left limb received intervention, while the right limb did not to allow for within-mouse comparison and adjustment of the measured variables. At the end of day 21, an average of 4 to 5 animals per group were included in the final tissue analysis.

Femoral Artery Ligation. The above-mentioned mice (The Jackson Laboratory, Bar Harbor, Me.), weighing 25 g to 30 g, were cared for and operated on after approval by the Institutional Animal Care and Use Committee guidelines at the University of Pennsylvania School of Medicine. Before surgery, mice were anesthetized using intraperitoneal injection of ketamine/xylazine cocktail (100 mg/kg ketamine Þ 10 mg/kg xylazine) at 0 1 mL/10 g body weight (0.25 mL to 0.30 mLpermouse). Femoral artery ligation was performed as previously described.7,8 Briefly, in a sterile fashion, the left femoral artery was exposed, isolated from the femoral nerve and vein, and ligated distally to the origin of the deep femoral artery, using a 6.0 silk sutures (Fisher Scientific, Pittsburgh, Pa.). The skin was then closed by interrupted 4.0 silk sutures (Fisher Scientific).

Plasmids. Immediately after left femoral artery ligation, the adductor muscle was injected with either the constitutively expressed HIF-1α plasmid DNA (modified and optimized) or pVAX plasmid DNA per manufacturer's specifications (GenScript USA Inc, Piscataway, N.J.) distal to the ligation site using an insulin syringe with a 30-gauge needle. Treatments were administered as follows: (1) IM injection of 20 mL (5 mg/mL) of HIF-1α plasmid DNA was administered in the left adductor muscle of the experimental group (HIF-EP) followed by EP; (2) IM injection of 20 mL (5 mg/mL) of HIF-1α plasmid DNA was administered in the left adductor muscle of the positive control group (HIF-IM); and (3) IM injection of 20 mL (5 mg/mL) of pVAX plasmid DNA was administered in the left adductor muscle of the negative control group (pVAXEP) followed by EP.

In Vivo EP. Immediately after plasmid DNA injection, in vivo square wave-pulse EP was administered to the treatment sites using the three-electrode array CELLECTRA DNA delivery device (Inovio Biomedical, Blue Bell, Pa.). The three-electrode array consists of three 26-gauge solid stainless steel electrodes in an isosceles triangle formation. The specific EP conditions were set constant at a current of 0.1 amp, two pulses, 52 ms/pulse (50-100 V), and 4 seconds between pulses. The duration between plasmid injection and EP was 20 seconds. The sequence of events for plasmid injection/EP was as follows: (1) the disposable electrode assembly is placed in the receptacle of the handle, and the initiation button on the handle is pressed; (2) IM injection of 20 mL (5 mg/mL) of HIF-1a plasmid DNA is administered using an insulin syringe with a 30-gauge needle; (3) immediately, the three array needles are placed into the area surrounding the injection site; (4) the initiation button on handle is then pressed, and after a 4-second countdown, pulse is delivered. The arrays are then gently removed from the muscle. The same sequence was repeated for the pVAX-EP group.

Limb Perfusion Measurement. Baseline limb perfusion measurements were performed preoperatively using laser Doppler perfusion imager (LDPI) and repeated immediately postsurgical ligation of the femoral artery. Briefly, serial perfusion measurements were performed at each time point using LDPI (Moor Instruments Inc, Wilmington, Del.). The perfusion ratio was calculated (ligated/nonligated limb) and averages obtained for each mouse at each time point. The perfusion signal was displayed in codes ranging from (0) to (1000).

Foot Movement and Necrosis Scores. To assess functional recovery of hindlimb, a scoring system based on active foot movement was done serially by a blinded observer unaware of the treatment groups at each time point, using touch. Briefly, scoring was performed as follows: score 0, no leg use; score 1, use of the leg; score 2, active foot use; score 3, use of complete foot or spreading of the toes; and score 4, unrestricted movement. Additionally, the severity of necrosis was scored by a similarly blinded observer to assess mice that require euthanasia at each time point. Briefly, scoring was performed as follows: score 0, no necrosis; score 1, cyanosis/discoloration; score 2, necrosis/loss of one to two toes; score 3, necrosis/loss of three to five toes; score 4, severe necrosis (extending to dorsum pedis or higher). Mice scoring >3 or with limb autoamputation were euthanized.

Tissue Harvest and Immunohistochemistry for Necrosis and Angiogenesis. Tissue harvest and morphometric analysis were performed on day 21 for necrosis analysis. Immunohistochemistry for capillary growth and collateral vessel formation/remodeling were performed. Briefly, mice were sacrificed by $CO_2$ inhalation and perfused intracardially with phosphate-buffered saline followed by 4% paraformaldehyde. The adductor muscles were dissected, fixed in 4% paraformaldehyde for 48 hours, and embedded in paraffin before sectioning using cryostat (section of 10-15 mm) For morphometric analysis, sections were stained with hematoxylin and eosin and mounted on Fluoromount-G media (Southern Biotech, Birmingham, Ala.) to evaluate for percent tissue necrosis Immunofluorescent staining was performed. Briefly, staining for CD31 was performed using mouse monoclonal antibody against human CD31 (Dako Cytomation, Inc, Carpentaria, Calif.) and counterstained with Texas Red fluorescent dye (Gene Link Inc, Hawthorne, N.Y.) to detect vascular endothelial cells. Mouse monoclonal antibodies against a-SMA (Research Diagnostics Inc, Flanders, N.J.) was used and was counterstained with Alexa 568 fluorescent dye (Life Technologies, Grand Island, N.Y.) to detect vascular smooth muscle cells. Irradiation with microwave was performed for antigen retrieval. Sections were incubated in 0.3% hydrogen peroxide to block peroxidase activity. Protein blocking, incubation with secondary biotinylated antibody, and avatin-biotin interaction were performed using the Vectastain kit (Vector Laboratories, Burlingame, Calif.). Quantification for necrosis, capillary growth, and collateral vessel formation were done on an average of five randomly selected fields at ×200 magnification per tissue slide and analysis performed using Image J software.

Statistical Analysis. Summary statistics are presented as sample size and mean±standard error of mean. Calculated variables for analysis include LDPI ratios for each image and average LDPI ratio per mouse at each time point. Concurrently, clinical foot movement, necrosis score, and immunohistochemical analysis results were assessed. The data follow a two-factor mixed-effects experimental design with one repeated factor (day) and one nonrepeated factor (treatment). Recognizing the presence of effect modification of treatment with advancing days following surgery, simple effects of treatment on continuous response variables was assessed by an analysis of variance appropriate for a one-way fixed-effect model for each day. When statistically significant differences were found among treatment groups, differences between pairwise comparisons of treatment groups were assessed by application of Bonferonni adjustment for multiple comparisons for each day. When assumptions for analysis of variance appeared to be unreasonable, the Wilcoxon rank-sum nonparametric test was performed. Contingency tables of limb necrosis score vs treatment group were analyzed by Pearson uncorrected $\chi^2$ test to assess distribution of limb necrosis score differences among the treatment groups. For all tests of hypothesis, type I error (a) was fixed at 0.05 for declaring statistical significance. All analyses were performed using STATA (Intercooled), version 11 statistical software (STATACorp, LP, College Station, Tex.).

Example 2

In Vivo EP of HIF-1α DNA and Limb Blood Flow Recovery

Limb blood flow recovery was examined in the ischemic tissue of mice receiving in vivo-EP mediated delivery of HIF-1α DNA plasmid and IM delivery of HIF-1α DNA plasmid.

Figure 3:
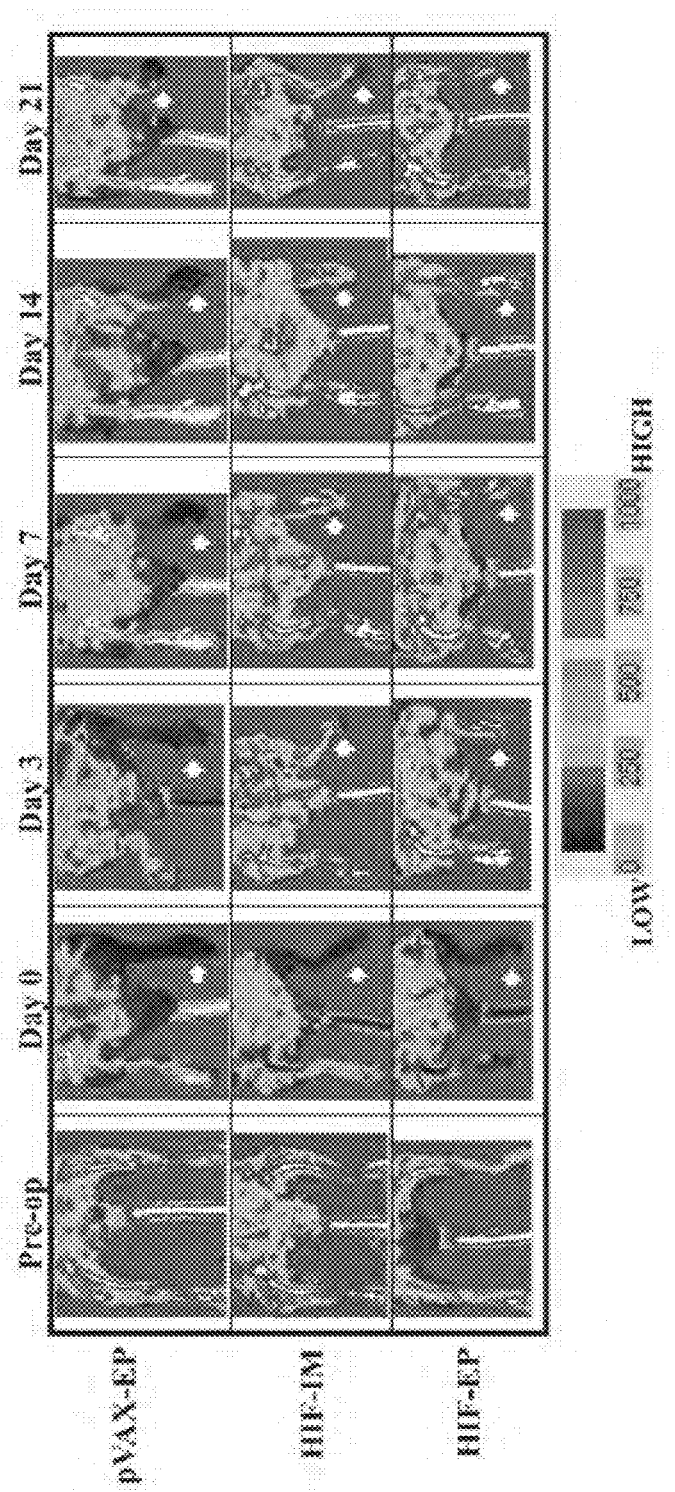
FIG. 3 shows (A) representative images recorded with a laser Doppler perfusion imager; (B) a graph plotting days post femoral artery ligation vs. limb perfusion ratio (ligated/non-ligated); (C) a graph plotting days post femoral artery ligation vs. limb movement score; and (D) a graph plotting treatment group vs. percent limb necrosis score less than three.
Figure 4:
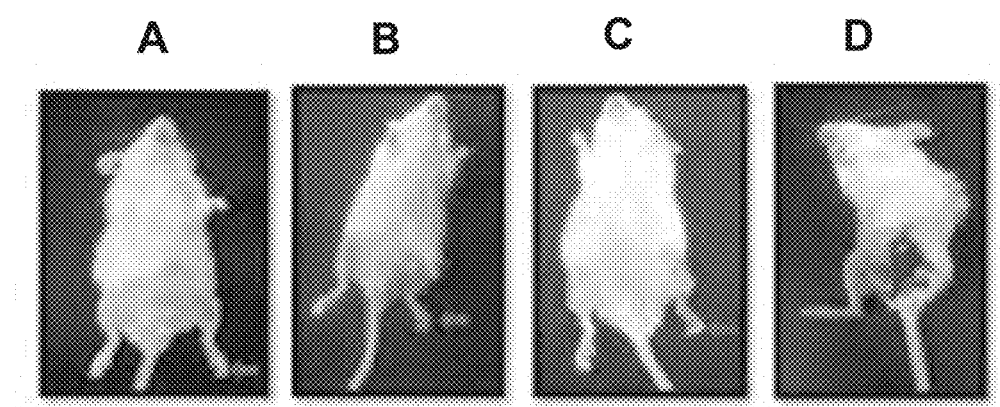
FIG. 4 shows gross depiction of hind limb recovery post-surgery in (A) mice treated with the combination of DNA encoding HIF-1α and electroporation (EP); (B) mice treated with intramuscular (IM) injection of DNA encoding HIF-1α; (C) mice treated with the combination of pVAX1 DNA (empty vector control) and EP; and (D) sham treated limb. In each of FIGS. 4A-4D, the arrow indicated the affected limb.

FIG. 3A shows a time course of hindlimb blood flow after femoral artery ligation followed by either electroporation (EP) of injected plasmid (hypoxia-inducible factor-EP [HIF-EP] and empty backbone plasmid DNA-EP [pVAX-EP]) or injected plasmid alone (hypoxia-inducible factor-intramuscular injection [HIF-IM]). In FIG. 3A, the representative laser Doppler perfusion imager (LDPI) were recorded on the days indicated and the perfusion signal was displayed in codes, namely poor perfusion was (0) and good perfusion was (1000).

An acute reduction in blood flow was apparent in the left limb (ligated, white arrows), on day 0 after femoral artery ligation (FIG. 3A). Accordingly, these LDPI measurements showed acutely reduced flow in the ligated limbs as compared with nonligated limbs on day 0, consistent with successful femoral artery ligation (FIG. 3A). Sustained blood flow recovery was observed in the group treated with HIF-EP as compared with the other two groups (HIF-IM and pVAX-EP) (FIG. 3A).

Furthermore, serial LDPI measurements revealed steady blood flow recovery in the ligated limbs, but at variable rates and consistency. Blood flow recovery was evident on days 3 through day 7 in the active treatment group (HIF-EP) and in the positive control group (HIFIM). Recovery decreased in both groups on day 14, but it increased on day 21. Overall, HIF-EP mice had similar flow recovery from day 3 to day 14 as compared with HIF-IM mice.

FIG. 3B shows that treatment with hypoxia-inducible factor 1 alpha (HIF-1α) DNA followed by EP improved limb perfusion recovery postfemoral artery ligation in mice. Limb perfusion recovery was performed serially from the preoperative day through postoperative day 21 using LDPI. Mean perfusion ratios (ligated/nonligated limb) were calculated for each mouse at each time point and for each treatment group. The data were expressed as mean±standard error of the mean (error bars across each animal) for statistical significance through day 21 ($P<0.05$). *HIF-EP vs pVAX-EP; $P<0.001$; **HIF-IM vs pVAX-EP; $P<0.01$; and $^a$HIF-EP vs HIF-IM; $P<0.05$. Significant improvement in limb blood flow between HIF-EP and HIF-IM was detected on day 21 (1.03±0.15 vs 0.78±0.064; FIG. 3B). Blood flow recovery was maintained at a much slower rate in the pVAX-EP group.

Example 3

Limb Function Recovery and In Vivo EP of HIF-1α DNA

Limb function recovery was examined in the ischemic tissue of mice receiving in vivo-EP mediated delivery of HIF-1α DNA plasmid and IM delivery of HIF-1α DNA plasmid.

FIGS. 4A, 4B, 4C, and 4D show the recovery of critical limb ischemia post femoral artery ligation and treatment with HIF-EP, HIF-IM, pVAX-EP, and normal, sham treated limb, respectively. FIG. 3C shows that clinical foot movement was improved post-femoral artery ligation in mice treated with HIF-1α DNA followed by EP. Foot movement was determined and scored 0 to 4 as a functional readout parameter to assess functional deficit after ischemia induction. Active foot movement was significantly impaired in pVAX-EP mice but significantly improved in the HIF-EP mice on day 21. The data were mean±standard error of the mean (error bars across each mice) for statistical significance ($P<0.05$). *HIF-EP vs pVAX-EP; $P<0.001$; **HIF-IM vs pVAX-EP; $P<0.01$; and $^a$HIF-EP vs HIF-IM; $P<0.05$.

These data showed that there was acute limb functional impairment on day 0 for all three treatment groups. HIF-EP and HIF-IM mice displayed similar improvement in limb function spanning days 3 through 14. Statistically significant difference in foot movement score was seen on day 21 (3.5±0.58 vs 2.4±1.14; $P<0.05$), in which the foot movement score was significantly higher from HIF-EP mice as compared to HIF-IM mice . The pVAX-EP mice displayed the worst limb function recovery all through day 21 (FIG. 3C).

Example 4

In Vivo EP of HIF-1α DNA and Limb Necrosis

Limb necrosis was examined in the ischemic tissue of mice receiving in vivo-EP mediated delivery of HIF-1α DNA plasmid and IM delivery of HIF-1α DNA plasmid.

FIG. 3D shows that clinical limb necrosis score was improved over 21 days in mice treated with HIF-1α followed by EP. A clinical scoring system from 0 to 4 was used to determine the rate of limb necrosis post-femoral artery ligation, and mice with scores ≥3 were deemed to have severe necrosis and were euthanized. More pVAX-EP mice had limb necrosis >3, thus requiring euthanasia, when compared with HIF-EP and HIF-IM mice. Data are summarized as mean±standard error of the mean (error bars) for the 39 mice through day 21, (HIF-EP, n=13; HIF-IM, n=14; pVAX-EP, n=12), statistical significance at $P<0.05$.

These data showed that limb functional recovery correlated with degree of necrosis and/or need for euthanasia due to severe necrosis or autoamputation. HIF-EP mice showed the lowest rate of limb necrosis (limb necrosis score <3) and auto-amputation requiring euthanasia as compared with HIF-IM mice (77% 6 12% vs 43% 6 14%; $P<0.05$) and HIF-EP compared with pVAX-EP (77% 6 12% vs 17% 6 11%; $P<0.01$; FIG. 3D).

Example 5

Tissue Necrosis, Capillary Density, Collateral Vessels, and Vascular Area

Tissue necrosis, capillary density, collateral vessels, and vascular area were examined in the ischemic tissue of mice receiving in vivo-EP mediated delivery of HIF-1α DNA plasmid and IM delivery of HIF-1α DNA plasmid.

Figure 5:
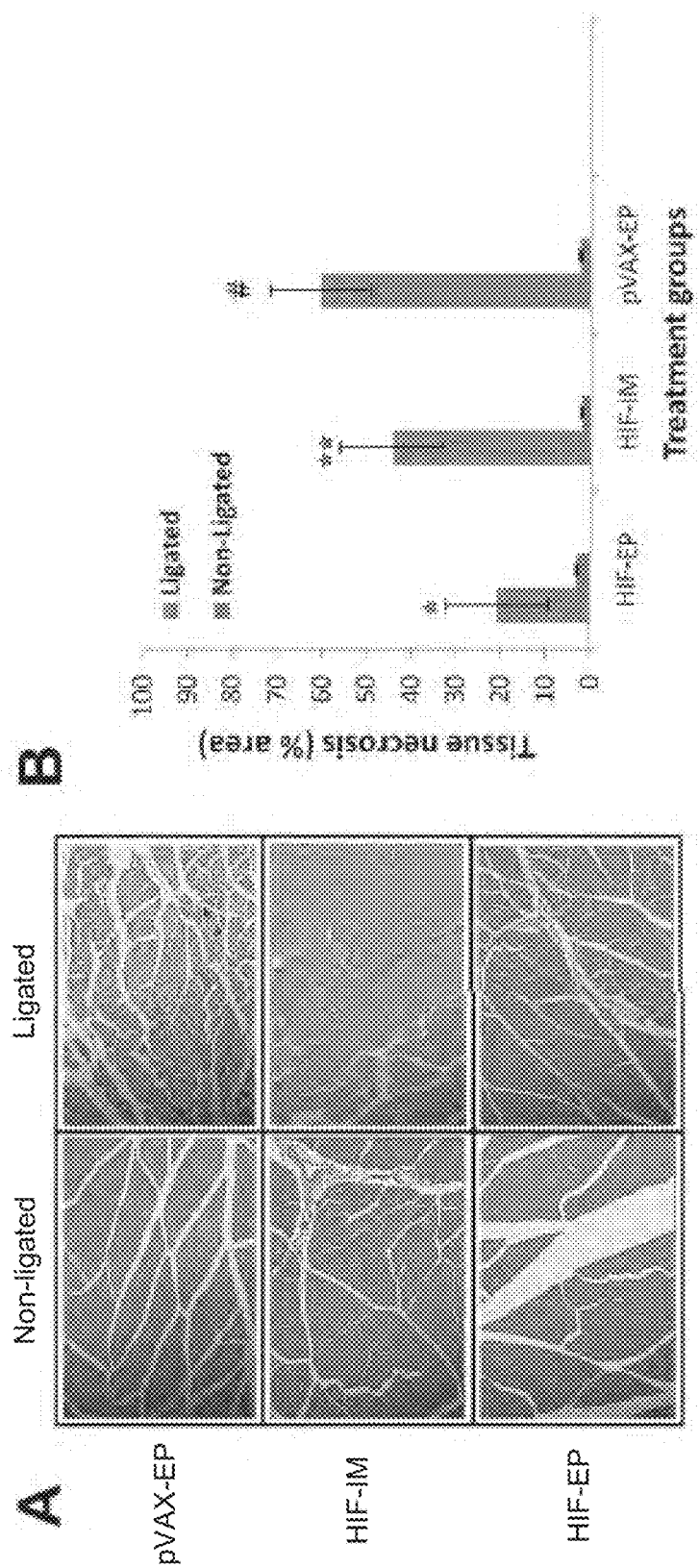
FIG. 5 shows (A) representative photomicrographs (original magnification, ×200) of adductor muscle tissue sections stained with hematoxylin and eosin (H&E); (B) a graph plotting treatment group vs. tissue necrosis (percent area); (C) representative photomicrographs (original magnification, ×200) of adductor muscle tissue stained for CD31+ capillaries; and (d) a graph plotting treatment group vs. capillary density (CD31+ cells/HPF).

Representative photomicrographs of adductor muscles tissue sections stained on day 21 with hematoxylin and eosin and immunofluorescence dyes for necrosis, CD31-positive endothelial cells, and α-SMA-positive vessels are shown in FIGS. 5A and 5C, respectively. FIG. 5A shows representative photomicrographs (original magnification, ×200) of adductor muscle tissue sections stained with hematoxylin and eosin (H&E) on day 21 revealing that there were more necrotic tissue areas in the ligated muscles in the negative control group (empty backbone plasmid DNA-electroporation [pVAX-EP]), compared with the positive control group (hypoxia-inducible factor-intramuscular injection [HIF-IM]). There was less necrotic infiltrating inflammatory cells in the active treatment group (HIF-EP).

FIG. 5C shows representative photomicrograph (original magnification, ×200) of adductor muscle tissue stained for CD31+ capillaries on day 21 to quantify capillary density. The number of CD31+ capillaries) was more in the ligated limb muscles that received HIF-EP treatment as compared with those that received negative control therapy (pVAX-EP) and positive control (HIF-IM).

FIG. 5B shows that the summarized quantitative data revealed significantly fewer percent areas of necrotic tissues in the active treatment group (HIF-EP) as compared with the positive control group (HIF-IM) and the negative control group (pVAX-EP). Data presented as mean±standard error of the mean (error bars) at statistical significance set at $P<0.05$. *$P<0.001$ (HIF-EP vs HIF-IM); **$P<0.01$ (HIF-IM vs pVAX-EP); and #$P<0.0001$ (HIF-EP vs pVAX-EP). The HIF-EP mice had less adductor muscle necrosis compared with the control mice at day 21 (HIF-EP vs HIF-IM, 20.7%±1.75% vs 44%±3.73%; $P<0.001$; HIF-EP vs pVAX-EP, 20.7%±1.75% vs 60.05%±2.17%; $P<0.0001$; and HIF-IM vs pVAX-EP, 44%±3.73% vs 60.05%±2.17%; $P<0.01$; FIG. 5B).

FIG. 5D shows a quantitative data summary that demonstrated that CD31+ capillaries were significantly higher in the active treatment group (HIF-EP) compared with the negative control group (pVAX-EP) and the positive control group (HIF-IM). Data presented as mean±standard error of the mean, statistical significance at $P<0.05$. *$P<0.001$ (HIF-EP vs HIF-IM); **$P<0.001$ (HIF-IM vs pVAX-EP); and #$P<0.0001$ (HIF-EP vs pVAX-EP). Capillary density (CD31+ endothelial cells) increased in adductor muscles of HIF-EP mice compared with the control groups (HIF-EP vs HIF-IM, 96.83±5.72 vessels/high-powered field [hpf] vs 62.87±2.0 vessels/hpf; $P<0.001$; HIF-EP vs pVAX-EP, 96.83±5.72 vessels/hpf vs 39.37±2.76 vessels/hpf; $P<0.0001$; and HIF-IM vs pVAX/EP, 62.87±2.0 vessels/hpf vs 39.37±2.76 vessels/hpf; $P<0.001$; FIG. 5D).

Figure 6:
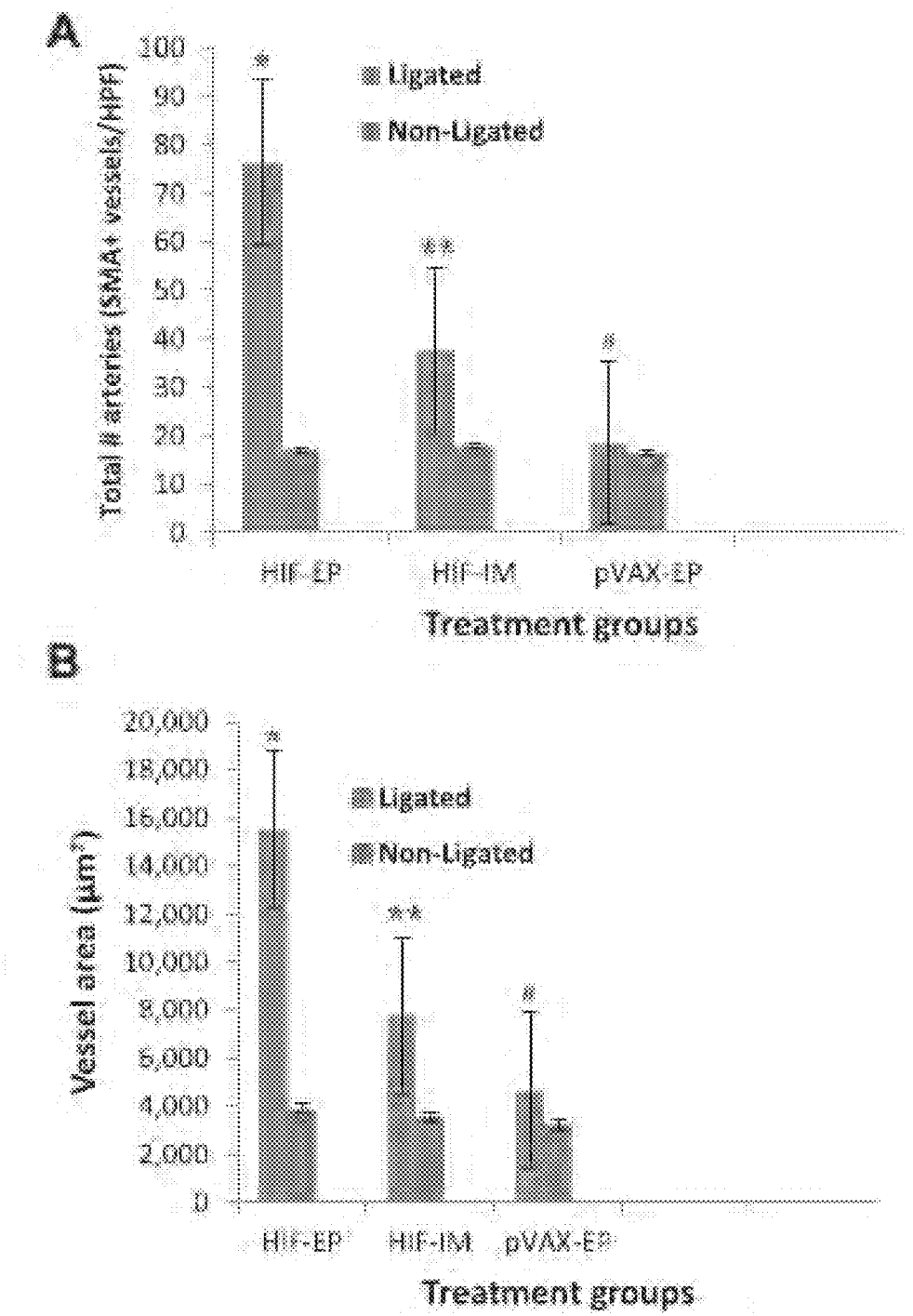
FIG. 6 shows graphs plotting (A) treatment group vs. total number arteries (SMA+ vessels/HPF); and (B) treatment group vs. vessel area ($\mu m^2$).

FIG. 6A depicts summarized quantitative data showing that smooth muscle actin (SMA)+ vessels (vascular remodeling/collaterals) were significantly higher in the active treatment group (hypoxia inducible factor-electroporation [HIF-EP]) compared with the negative control group (empty backbone plasmid DNA-EP [pVAX-EP]) and the positive control group (hypoxia-inducible factor-intramuscular injection [HIF-IM]). Data presented as mean±standard error of the mean, statistical significance at $P<0.05$. *$P<0.0001$ (HIF-EP vs HIF-IM); **$P<0.0001$ (HIF-IM vs pVAX-EP); and #$P<0.001$ (HIF-EP vs pVAX-EP). Collateral vessels number/vessel remodeling was also increased in the HIF-EP mice compared with the control groups (HIF-EP vs HIF-IM, 76.33±1.94 vessels/hpf vs 37.5±1.56 vessels/hpf; $P<0.0001$; HIF-EP vs pVAXEP, 76.33±1.94 vessels/hpf vs 18.5±1.34 vessels/hpf; $P<0.00001$; and HIF-IM vs pVAX-EP, 37.5±1.56 vessels/hpf vs 18.5±1.34 vessels/hpf; $P<0.001$; FIG. 6A).

FIG. 6B depicts a quantitative data summary that demonstrated that the SMA+ vessels were significantly larger in total area ($\mu m^2$) in the active treatment group (HIF-EP) compared with the negative control group (pVAX-EP) and the positive control group (HIF-IM). Statistical significance was set at $P<0.05$. *$P<0.001$ (HIF-EP vs HIF-IM); **$P<0.05$ (HIF-IM vs pVAX-EP); and #$P<0.0001$ (HIF-EP vs pVAX-EP). Total vessel area was larger in the HIF-EP compared with the controls (HIF-EP vs HIF-IM, 15,521.67±1298.16 $\mu m^2$ vs 7788.87±392.04 $\mu m^2$; $P<0.001$; HIF-EP vs pVAX-EP, 15,521.67±1298.16 $\mu m^2$ vs 4640.25±614.01 $\mu m^2$; $P<0.0001$; and HIF-IM vs pVAX-EP, 7788.87±392.04 $\mu m^2$ vs 4640.25±614.01 $\mu m^2$; $P<0.05$; FIG. 6B).

Example 6

Summary of Results from Examples 2-5

In summary of the above investigation, in vivo EP-mediated delivery of HIF-1α plasmid DNA improved neovascularizastion in the mouse model of limb ischemia. Specifically, the investigation demonstrated that in vivo EP of HIF-1α DNA significantly improved limb perfusion (HIF-EP: 1.03±0.15 vs HIF-IM: 0.78±0.064; $P<0.05$, vs pVAX-EP: 0.41±0.019; $P<0.001$), limb functional recovery (HIF-EP: 3.5±0.58 vs HIF-IM, 2.4±1.14; $P<0.05$, vs pVAX-EP: 2.4±1.14; $P<0.001$), and limb autoamputation on day 21 (HIF-EP: 77%±12% vs HIF-IM: 43%±14%; $P<0.05$ vs pVAX-EP: 17%±11%; $P<0.01$).

The investigation also demonstrated that adductor muscle tissue necrosis was decreased (HIF-EP: 20.7%±1.75% vs HIF-IM: 44%±3.73; $P<0.001$, vs pVAX-EP: 60.05%±2.17%; $P<0.0001$), capillary density was increased (HIF-EP: 96.83±5.72 vessels/high-powered field [hpf] vs HIF-IM: 62.87±2.0 vessels/hpf; $P<0.001$, vs pVAX-EP: 39.37±2.76 vessels/hpf; $P<0.0001$), collateral vessel formation was increased (HI-EP: 76.33±1.94 vessels/hpf vs HIF-IM: 37.5±1.56 vessels/hpf; $P<0.0001$, vs pVAX-EP: 18.5±1.34 vessels/hpf; $P<0.00001$), and the vessels were larger (HIF-EP: 15,521.67±1298.16 $\mu m^2$ vs HIF-IM: 7788.87±392.04 $\mu m^2$; $P<0.001$ vs pVAX-EP: 4640.25±614.01 $\mu m^2$; $P<0.0001$).

Accordingly, these data demonstrated statistically significant improvement in limb perfusion recovery, physiological limb function, and improved vascularity at the capillary level, vascular remodeling, and tissue morphologic features in the mice receiving in vivo EP-mediated delivery of HIF-1a plasmid DNA through the endpoint of the study (i.e., day 21). Mice receiving IM delivery of HIF-1a plasmid DNA did not maintain these gains through the endpoint of the study (i.e., day 21). These data also demonstrated that mice receiving in vivo EP-mediated delivery of HIF-1α plasmid DNA had significantly lower rates of limb necrosis and auto-amputation.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof

What is claimed is:

1. A therapeutic comprising a nucleic acid molecule comprising a nucleotide sequence encoding an Immunoglobulin E (IgE) leader sequence and hypoxia inducible factor-1 alpha (HIF+1α), wherein said nucleic acid molecule comprises at least one nucleotide sequence selected from the group consisting of SEQ ID NO:3, and SEQ ID NO:5.

2. The therapeutic of claim 1, further comprising a pharmaceutically acceptable excipient.

3. A method of treating hypoxia or ischemia in a subject in need thereof, the method comprising administering the therapeutic of claim 1 to the subject.

4. The method of claim 3, wherein administering the therapeutic includes electroporation.

5. The method of claim 3, wherein administering the therapeutic includes at least one of intramuscular administration and intradermal administration.

6. The method of claim 3, wherein the hypoxia or ischemia is associated with critical limb ischemia, peripheral artery disease, wound healing, a vascular disease, a circulatory disease, coronary artery disease, cardiovascular disease, or diabetes.

7. The method of claim 6, wherein the hypoxia or ischemia is associated with critical limb ischemia.

8. The method of claim 3, wherein at least one of capillary density, collateral vessel formation or vessel size is increased in the subject administered the therapeutic as compared to a subject not administered the therapeutic.

9. The method of claim 3, wherein tissue perfusion is increased in the subject administered the therapeutic as compared to a subject not administered the therapeutic.

10. The method of claim 3, wherein tissue necrosis is decreased in the subject administered the therapeutic as compared to a subject not administered the therapeutic.

11. A nucleic acid molecule comprising a nucleotide sequence selected from the group consisting of: the nucleotide sequence of SEQ ID NO:5, and the nucleotide sequence of SEQ ID NO:3, wherein said nucleic acid molecule further comprises a nucleotide sequence comprising encoding an Immunoglobulin E (IgE) leader sequence.

12. The nucleic acid molecule of claim 11, wherein the nucleotide sequence is a plasmid.

* * * * *

SEQUENCE LISTING

<160> NUMBER OF SEQ ID NOS: 6

<210> SEQ ID NO 1
<211> LENGTH: 2523
<212> TYPE: DNA
<213> ORGANISM: Artificial Sequence
<220> FEATURE:
<223> OTHER INFORMATION: Mouse HIF-1 alpha with P to A substitutions and IgE leader sequence

<400> SEQUENCE: 1

```
atggattgga cttggatctt attttagtt gctgctgcta ctagagttca ttctgagggg    60
gctgagggg agaacgaaaa aagaaaatg tcatctgaga gacgaaagga aaaatcacgg   120
gacgccgcac gaagtagaag gacaaaggaa tctgaggtgt tctacgagct ggcccaccag   180
ctgcctctcc cacacaacgt gagctcccat ctggacaagg cttcagtcat gagactgacc   240
attagctatc tcagggtgag aaaactgctc gatgctggcg gactggatag cgaagacgag   300
atgaaggccc agatggattg cttctacctg aaagctctcg acgggtttgt gatggtcctg   360
acagacgatg cgacatggt gtacatcagt gacaacgtca ataagtatat gggcctgacc   420
cagtttgagc tcgccggaca ctccgtgttc gacttcaccc acccttgcga ccatgaggaa   480
atgcgggaaa tgctgactca tcgcaacggg ccagtccgaa agggtaaaga gctgaatacc   540
cagaggagct tctttctgag aatgaagtgt acactcacta gtcggggccg cactatgaac   600
attaagtcag ccacctggaa agtgctgcat tgcacaggcc acatccatgt ctacgacacc   660
aactccaatc agcctcagtg tggatataag aaacccccta tgacatgcct ggtgctcatt   720
tgtgaaccca tccctcaccc atccaatatc gagattccac tggactctaa gacattcctg   780
tcaagacata gcctcgatat gaaattttcc tactgcgacg aacggattac tgagctgatg   840
gggtatgaac ccgaggaact gctcggtagg agcatctacg agtactatca cgccctggat   900
tccgaccatc tcaccaagac acaccatgac atgttcacaa aaggccaggt gaccacagga   960
cagtaccgga tgctggctaa acgcggggt tacgtgtggg tcgagactca ggcaaccgtg  1020
atctacaaca ctaagaattc tcagcccag tgcatcgtgt gcgtgaacta cgtggtcagt  1080
ggaatcattc agcacgacct gctcttttct ctgcagcaga ccgaaagtgt gctcaagcct  1140
gtcgagtcta gtgatatgaa gatgacccag ctgttcacaa agtggaaag tgaggataca  1200
tcatgtctgt ttgacaagct caagaaagag ccagacgctc tgactctgct cgcagctgca  1260
gcaggcgata ccatcattag tctggacttc ggatcagacg atactgaaac cgaggatcag  1320
cagctggaag acgtgcctct ctacaacgac gtgatgtttc catcaagcaa tgagaagctg  1380
aacatcaatc tcgccatgag cccccctgcct tcctctgaaa ccccaaaacc cctgcggagt  1440
tcagctgatc ccgcactgaa ccaggaggtg gctctgaagc tcgaaagctc ccccgagagc  1500
ctgggactct ccttcactat gcctcagatc caggatcagc ccgcaagtcc ttcagacggg  1560
tctacccgcc agtctagtcc tgaaccaaac agcccttccg agtattgctt cgatgtggac  1620
agcgatatgg tgaatgtctt caagctggaa ctcgtcgaga aactgtttgc agaagacacc  1680
gaggccaaga accccttcag cacacaggac actgatctgg acctggagat gctggctgca  1740
tacattccca tggacgatga cttccagctg aggagctttg atcagctgag ccccctggag  1800
tctaatagtc catcaccacc cagcatgtcc acagtgactg gcttccagca gacacagctg  1860
cagaagccaa ccatcacagc aactgccact accacagcaa ctaccgacga atccaagacc  1920
gagacaaagg ataacaaaga ggacatcaaa attctgatcg cctctccctc aagcacccag  1980
gtgcctcagg aaacaactac cgctaaagca tccgcctatt ctgggactca ctctagaacc  2040
gctagtcccg atagagcagg caagagagtg atcgagcaga ctgacaaggc acatcctcga  2100
tcactgaaac tcagcgccac cctgaaccag aggaatacag tgccagagga agagctgaac  2160
cccaagacca ttgcctcaca gaatgctcag cgaaagagga aaatggagca cgacgggagc  2220
```

```
ctgttccagg cagctggaat cggaacactg ctccagcagc caggcgattg tgcccccact    2280
atgtctctga gttggaagcg cgtgaaaggc tttatttcct ctgaacagaa cggaacagag    2340
cagaagacta tcattctgat cccttccgat ctcgcttgcc gactgctcgg gcagtccatg    2400
gacgaatctg gtctgccaca gctcaccctct tacgattgtg aagtgaatgc ccccatccag    2460
ggtagccgaa atctcctcca gggtgaagaa ctgctcagag cactcgacca ggtgaactga    2520
taa                                                                  2523
```

<210> SEQ ID NO 2
<211> LENGTH: 839
<212> TYPE: PRT
<213> ORGANISM: Artificial Sequence
<220> FEATURE:
<223> OTHER INFORMATION: Mouse HIF-1 alpha with P to A substitutions and
      IgE leader sequence

<400> SEQUENCE: 2

```
Met Asp Trp Thr Trp Ile Leu Phe Leu Val Ala Ala Thr Arg Val
1               5                   10                  15

His Ser Glu Gly Ala Gly Gly Glu Asn Glu Lys Lys Lys Met Ser Ser
            20                  25                  30

Glu Arg Arg Lys Glu Lys Ser Arg Asp Ala Ala Arg Ser Arg Arg Thr
        35                  40                  45

Lys Glu Ser Glu Val Phe Tyr Glu Leu Ala His Gln Leu Pro Leu Pro
    50                  55                  60

His Asn Val Ser Ser His Leu Asp Lys Ala Ser Val Met Arg Leu Thr
65                  70                  75                  80

Ile Ser Tyr Leu Arg Val Arg Lys Leu Leu Asp Ala Gly Gly Leu Asp
                85                  90                  95

Ser Glu Asp Glu Met Lys Ala Gln Met Asp Cys Phe Tyr Leu Lys Ala
            100                 105                 110

Leu Asp Gly Phe Val Met Val Leu Thr Asp Asp Gly Asp Met Val Tyr
        115                 120                 125

Ile Ser Asp Asn Val Asn Lys Tyr Met Gly Leu Thr Gln Phe Glu Leu
    130                 135                 140

Ala Gly His Ser Val Phe Asp Phe Thr His Pro Cys Asp His Glu Glu
145                 150                 155                 160

Met Arg Glu Met Leu Thr His Arg Asn Gly Pro Val Arg Lys Gly Lys
                165                 170                 175

Glu Leu Asn Thr Gln Arg Ser Phe Phe Leu Arg Met Lys Cys Thr Leu
            180                 185                 190

Thr Ser Arg Gly Arg Thr Met Asn Ile Lys Ser Ala Thr Trp Lys Val
        195                 200                 205

Leu His Cys Thr Gly His Ile His Val Tyr Asp Thr Asn Ser Asn Gln
    210                 215                 220

Pro Gln Cys Gly Tyr Lys Lys Pro Pro Met Thr Cys Leu Val Leu Ile
225                 230                 235                 240

Cys Glu Pro Ile Pro His Pro Ser Asn Ile Glu Ile Pro Leu Asp Ser
                245                 250                 255

Lys Thr Phe Leu Ser Arg His Ser Leu Asp Met Lys Phe Ser Tyr Cys
            260                 265                 270

Asp Glu Arg Ile Thr Glu Leu Met Gly Tyr Glu Pro Glu Glu Leu Leu
        275                 280                 285

Gly Arg Ser Ile Tyr Glu Tyr Tyr His Ala Leu Asp Ser Asp His Leu
```

-continued

```
                290                 295                 300
Thr Lys Thr His His Asp Met Phe Thr Lys Gly Gln Val Thr Thr Gly
305                 310                 315                 320
Gln Tyr Arg Met Leu Ala Lys Arg Gly Gly Tyr Val Trp Val Glu Thr
                325                 330                 335
Gln Ala Thr Val Ile Tyr Asn Thr Lys Asn Ser Gln Pro Gln Cys Ile
                340                 345                 350
Val Cys Val Asn Tyr Val Val Ser Gly Ile Ile Gln His Asp Leu Leu
                355                 360                 365
Phe Ser Leu Gln Gln Thr Glu Ser Val Leu Lys Pro Val Glu Ser Ser
370                 375                 380
Asp Met Lys Met Thr Gln Leu Phe Thr Lys Val Glu Ser Glu Asp Thr
385                 390                 395                 400
Ser Cys Leu Phe Asp Lys Leu Lys Lys Glu Pro Asp Ala Leu Thr Leu
                405                 410                 415
Leu Ala Ala Ala Ala Gly Asp Thr Ile Ile Ser Leu Asp Phe Gly Ser
                420                 425                 430
Asp Asp Thr Glu Thr Glu Asp Gln Gln Leu Glu Asp Val Pro Leu Tyr
                435                 440                 445
Asn Asp Val Met Phe Pro Ser Ser Asn Glu Lys Leu Asn Ile Asn Leu
450                 455                 460
Ala Met Ser Pro Leu Pro Ser Ser Glu Thr Pro Lys Pro Leu Arg Ser
465                 470                 475                 480
Ser Ala Asp Pro Ala Leu Asn Gln Glu Val Ala Leu Lys Leu Glu Ser
                485                 490                 495
Ser Pro Glu Ser Leu Gly Leu Ser Phe Thr Met Pro Gln Ile Gln Asp
                500                 505                 510
Gln Pro Ala Ser Pro Ser Asp Gly Ser Thr Arg Gln Ser Ser Pro Glu
                515                 520                 525
Pro Asn Ser Pro Ser Glu Tyr Cys Phe Asp Val Asp Ser Asp Met Val
                530                 535                 540
Asn Val Phe Lys Leu Glu Leu Val Glu Lys Leu Phe Ala Glu Asp Thr
545                 550                 555                 560
Glu Ala Lys Asn Pro Phe Ser Thr Gln Asp Thr Asp Leu Asp Leu Glu
                565                 570                 575
Met Leu Ala Ala Tyr Ile Pro Met Asp Asp Asp Phe Gln Leu Arg Ser
                580                 585                 590
Phe Asp Gln Leu Ser Pro Leu Glu Ser Asn Ser Pro Ser Pro Pro Ser
                595                 600                 605
Met Ser Thr Val Thr Gly Phe Gln Gln Thr Gln Leu Gln Lys Pro Thr
610                 615                 620
Ile Thr Ala Thr Ala Thr Thr Ala Thr Thr Asp Glu Ser Lys Thr
625                 630                 635                 640
Glu Thr Lys Asp Asn Lys Glu Asp Ile Lys Ile Leu Ile Ala Ser Pro
                645                 650                 655
Ser Ser Thr Gln Val Pro Gln Glu Thr Thr Ala Lys Ala Ser Ala
                660                 665                 670
Tyr Ser Gly Thr His Ser Arg Thr Ala Ser Pro Asp Arg Ala Gly Lys
                675                 680                 685
Arg Val Ile Glu Gln Thr Asp Lys Ala His Pro Arg Ser Leu Lys Leu
                690                 695                 700
Ser Ala Thr Leu Asn Gln Arg Asn Thr Val Pro Glu Glu Glu Leu Asn
705                 710                 715                 720
```

```
Pro Lys Thr Ile Ala Ser Gln Asn Ala Gln Arg Lys Arg Lys Met Glu
            725                 730                 735
His Asp Gly Ser Leu Phe Gln Ala Ala Gly Ile Gly Thr Leu Leu Gln
        740                 745                 750
Gln Pro Gly Asp Cys Ala Pro Thr Met Ser Leu Ser Trp Lys Arg Val
    755                 760                 765
Lys Gly Phe Ile Ser Ser Glu Gln Asn Gly Thr Glu Gln Lys Thr Ile
770                 775                 780
Ile Leu Ile Pro Ser Asp Leu Ala Cys Arg Leu Leu Gly Gln Ser Met
785                 790                 795                 800
Asp Glu Ser Gly Leu Pro Gln Leu Thr Ser Tyr Asp Cys Glu Val Asn
            805                 810                 815
Ala Pro Ile Gln Gly Ser Arg Asn Leu Leu Gln Gly Glu Glu Leu Leu
        820                 825                 830
Arg Ala Leu Asp Gln Val Asn
        835

<210> SEQ ID NO 3
<211> LENGTH: 2490
<212> TYPE: DNA
<213> ORGANISM: Artificial Sequence
<220> FEATURE:
<223> OTHER INFORMATION: Mouse HIF-1 alpha with P to A substitutions

<400> SEQUENCE: 3
ggatccgcca ccatggaggg ggctggaggg gagaacgaaa agaagaaaat gtcatctgag        60
agacgaaagg aaaaatcacg ggacgccgca cgaagtagaa ggacaaagga atctgaggtg       120
ttctacgagc tggcccacca gctgcctctc ccacacaacg tgagctccca tctggacaag       180
gcttcagtca tgagactgac cattagctat ctcagggtga aaaactgctc gatgctggc        240 ggactggata gcaagacga gatgaaggcc cagatggatt gcttctacct gaaagctctc       300
gacgggtttg tgatggtcct gacagacgat ggcgacatgg tgtacatcag tgacaacgtc       360
aataagtata tgggcctgac ccagtttgag ctcgccggac actccgtgtt cgacttcacc       420
cacccttgcg accatgagga aatgcgggaa atgctgactc atcgcaacgg ccagtccga        480 aagggtaaag agctgaatac ccagagagc ttctttctga gaatgaagtg tacactcact       540
agtcggggcc gcactatgaa cattaagtca gccacctgga agtgctgca ttgcacaggc       600 cacatccatg tctacgacac caactccaat cagcctcagt gtggatataa gaaaccccct       660 atgcacatgcc tggtgctcat tgtgaaccc atccctcacc catccaatat cgagattcca       720
ctggactcta agacattcct gtcaagacat agcctcgata tgaaattttc ctactgcgac       780
gaacggatta ctgagctgat ggggtatgaa cccgaggaac tgctcggtag agcatctac       840 gagtactatc acgccctgga ttccgaccat ctcaccaaga cacaccatga catgttcaca       900
aaaggccagg tgaccacagg acagtaccgg atgctggcta aacgcggggg ttacgtgtgg       960
gtcgagactc aggcaaccgt gatctacaac actaagaatt ctcagcccca gtgcatcgtg      1020
tgcgtgaact acgtggtcag tggaatcatt cagcacgacc tgctcttttc tctgcagcag      1080
accgaaagtg tgctcaagcc tgtcgagtct agtgatatga agatgaccca gctgttcaca      1140
aaagtggaaa gtgaggatac atcatgtctg tttgacaagc tcaagaaaga gccagacgct      1200
ctgactctgc tcgcagctgc agcaggcgat accatcatta gtctggactt cggatcagac      1260
gatactgaaa ccgaggatca gcagctgaa gacgtgcctc tctacaacga cgtgatgttt      1320
```

```
ccatcaagca atgagaagct gaacatcaat ctcgccatga gcccctgcc ttcctctgaa   1380 accccaaaac ccctgcggag ttcagctgat cccgcactga accaggaggt ggctctgaag   1440
ctcgaaagct ccccgagag cctgggactc tccttcacta tgcctcagat ccaggatcag   1500
cccgcaagtc cttcagacgg gtctacccgc cagtctagtc ctgaaccaaa cagcccttcc   1560
gagtattgct tcgatgtgga cagcgatatg gtgaatgtct tcaagctgga actcgtcgag   1620
aaactgtttg cagaagacac cgaggccaag aaccccttca gcacacagga cactgatctg   1680
gacctggaga tgctggctgc atacattccc atggacgatg acttccagct gaggagcttt   1740
gatcagctga gccccctgga gtctaatagt ccatcaccac ccagcatgtc cacagtgact   1800
ggcttccagc agacacagct gcagaagcca accatcacag caactgccac taccacagca   1860
actaccgacg aatccaagac cgagacaaag gataacaaag aggacatcaa aattctgatc   1920 gcctctcct caagcaccca ggtgcctcag gaaacaacta ccgctaaagc atccgcctat   1980
tctgggactc actctagaac cgctagtccc gatagagcag gcaagagagt gatcgagcag   2040
actgacaagg cacatcctcg atcactgaaa ctcagcgcca ccctgaacca gaggaataca   2100
gtgccagagg aagagctgaa ccccaagacc attgcctcac agaatgctca gcgaaagagg   2160
aaaatggagc acgacgggag cctgttccag gcagctggaa tcggaacact gctccagcag   2220
ccaggcgatt gtgccccac tatgtctctg agttggaagc gcgtgaaagg ctttatttcc   2280
tctgaacaga acgaacaga gcagaagact atcattctga tcccttccga tctcgcttgc   2340
cgactgctcg ggcagtccat ggacgaatct ggtctgccac agctcaccct ttacgattgt   2400
gaagtgaatg cccccatcca gggtagccga aatctcctcc agggtgaaga actgctcaga   2460
gcactcgacc aggtgaactg ataactcgag                                    2490

<210> SEQ ID NO 4
<211> LENGTH: 822
<212> TYPE: PRT
<213> ORGANISM: Artificial Sequence
<220> FEATURE:
<223> OTHER INFORMATION: Mouse HIF-1 alpha with P to A substitutions

<400> SEQUENCE: 4

Met Glu Gly Ala Gly Gly Glu Asn Glu Lys Lys Met Ser Ser Glu
1               5                   10                  15

Arg Arg Lys Glu Lys Ser Arg Asp Ala Ala Arg Ser Arg Arg Thr Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Gly Leu Asp Ser
65                  70                  75                  80

Glu Asp Glu Met Lys Ala Gln Met Asp Cys Phe Tyr Leu Lys Ala Leu
                85                  90                  95

Asp Gly Phe Val Met Val Leu Thr Asp Asp Gly Asp Met Val Tyr Ile
            100                 105                 110

Ser Asp Asn Val Asn Lys Tyr Met Gly Leu Thr Gln Phe Glu Leu Ala
        115                 120                 125

Gly His Ser Val Phe Asp Phe Thr His Pro Cys Asp His Glu Glu Met
    130                 135                 140

Arg Glu Met Leu Thr His Arg Asn Gly Pro Val Arg Lys Gly Lys Glu
145                 150                 155                 160
```

```
Leu Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Leu Phe
            340                 345                 350

Ser Leu Gln Gln Thr Glu Ser Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Cys Leu Phe Asp Lys Leu Lys Lys Glu Pro Asp Ala Leu Thr Leu Leu
385                 390                 395                 400

Ala Ala Ala Ala Gly Asp Thr Ile Ile Ser Leu Asp Phe Gly Ser Asp
                405                 410                 415

Asp Thr Glu Thr Glu Asp Gln Gln Leu Glu Asp Val Pro Leu Tyr Asn
            420                 425                 430

Asp Val Met Phe Pro Ser Ser Asn Glu Lys Leu Asn Ile Asn Leu Ala
        435                 440                 445

Met Ser Pro Leu Pro Ser Ser Glu Thr Pro Lys Pro Leu Arg Ser Ser
    450                 455                 460

Ala Asp Pro Ala Leu Asn Gln Glu Val Ala Leu Lys Leu Glu Ser Ser
465                 470                 475                 480

Pro Glu Ser Leu Gly Leu Ser Phe Thr Met Pro Gln Ile Gln Asp Gln
                485                 490                 495

Pro Ala Ser Pro Ser Asp Gly Ser Thr Arg Gln Ser Ser Pro Glu Pro
            500                 505                 510

Asn Ser Pro Ser Glu Tyr Cys Phe Asp Val Asp Ser Asp Met Val Asn
        515                 520                 525

Val Phe Lys Leu Glu Leu Val Glu Lys Leu Phe Ala Glu Asp Thr Glu
    530                 535                 540

Ala Lys Asn Pro Phe Ser Thr Gln Asp Thr Asp Leu Asp Leu Glu Met
545                 550                 555                 560

Leu Ala Ala Tyr Ile Pro Met Asp Asp Asp Phe Gln Leu Arg Ser Phe
                565                 570                 575
```

```
Asp Gln Leu Ser Pro Leu Glu Ser Asn Ser Pro Pro Ser Met
            580                 585                 590

Ser Thr Val Thr Gly Phe Gln Gln Thr Gln Leu Gln Lys Pro Thr Ile
        595                 600                 605

Thr Ala Thr Ala Thr Thr Thr Ala Thr Asp Glu Ser Lys Thr Glu
        610                 615                 620

Thr Lys Asp Asn Lys Glu Asp Ile Lys Ile Leu Ile Ala Ser Pro Ser
625                 630                 635                 640

Ser Thr Gln Val Pro Gln Glu Thr Thr Ala Lys Ala Ser Ala Tyr
                645                 650                 655

Ser Gly Thr His Ser Arg Thr Ala Ser Pro Asp Arg Ala Gly Lys Arg
        660                 665                 670

Val Ile Glu Gln Thr Asp Lys Ala His Pro Arg Ser Leu Lys Leu Ser
            675                 680                 685

Ala Thr Leu Asn Gln Arg Asn Thr Val Pro Glu Glu Leu Asn Pro
        690                 695                 700

Lys Thr Ile Ala Ser Gln Asn Ala Gln Arg Lys Arg Lys Met Glu His
705                 710                 715                 720

Asp Gly Ser Leu Phe Gln Ala Ala Gly Ile Gly Thr Leu Leu Gln Gln
                725                 730                 735

Pro Gly Asp Cys Ala Pro Thr Met Ser Leu Ser Trp Lys Arg Val Lys
        740                 745                 750

Gly Phe Ile Ser Ser Glu Gln Asn Gly Thr Glu Gln Lys Thr Ile Ile
        755                 760                 765

Leu Ile Pro Ser Asp Leu Ala Cys Arg Leu Leu Gly Gln Ser Met Asp
770                 775                 780

Glu Ser Gly Leu Pro Gln Leu Thr Ser Tyr Asp Cys Glu Val Asn Ala
785                 790                 795                 800

Pro Ile Gln Gly Ser Arg Asn Leu Leu Gln Gly Glu Glu Leu Leu Arg
                805                 810                 815

Ala Leu Asp Gln Val Asn
            820

<210> SEQ ID NO 5
<211> LENGTH: 2481
<212> TYPE: DNA
<213> ORGANISM: Artificial Sequence
<220> FEATURE:
<223> OTHER INFORMATION: Human HIF-1 alpha with P to A substitutions

<400> SEQUENCE: 5
atggagggcg ccggcggcgc gaacgacaag aaaaagataa gttctgaacg tcgaaaagaa      60
aagtctcgag atgcagccag atctcggcga agtaaagaat ctgaagtttt ttatgagctt     120
gctcatcagt tgccacttcc acataatgtg agttcgcatc ttgataaggc ctctgtgatg     180
aggcttacca tcagctattt gcgtgtgagg aaacttctgg atgctggtga tttggatatt     240
gaagatgaca tgaaagcaca gatgaattgc ttttatttga aagccttgga tggttttgtt     300
atggttctca cagatgatgg tgacatgatt tacatttctg ataatgtgaa caaatacatg     360
ggattaactc agtttgaact aactggacac agtgtgtttg attttactca tccatgtgac     420
catgaggaaa tgagagaaat gcttacacac agaaatggcc ttgtgaaaaa gggtaaagaa     480
caaaacacac agcgaagctt ttttctcaga atgaagtgta ccctaactag ccgaggaaga     540
actatgaaca taaagtctgc aacatggaag gtattgcact gcacaggcca cattcacgta     600
tatgatacca acagtaacca acctcagtgt gggtataaga aaccacctat gacctgcttg     660
```

-continued

```
gtgctgattt tgtgaacccat tcctcaccca tcaaatattg aaattcottt agatagcaag    720 actttcctca gtcgacacag cctggatatg aaatttctt attgtgatga aagaattacc    780
gaattgatgg gatatgagcc agaagaactt ttaggccgct caatttatga atattatcat    840
gctttggact ctgatcatct gaccaaaact catcatgata tgtttactaa aggacaagtc    900
accacaggac agtacaggat gcttgccaaa agaggtggat atgtctgggt tgaaactcaa    960
gcaactgtca tatataacac caagaattct caaccacagt gcattgtatg tgtgaattac    1020
gttgtgagtg gtattattca gcacgacttg attttctccc ttcaacaaac agaatgtgtc    1080
cttaaaccgg ttgaatcttc agatatgaaa atgactcagc tattcaccaa agttgaatca    1140
gaagatacaa gtagcctctt tgacaaactt aagaaggaac ctgatgcttt aactttgctg    1200
gccgcagccg ctggagacac aatcatatct ttagattttg gcagcaacga cacagaaact    1260
gatgaccagc aacttgagga agtaccatta tataatgatg taatgctccc ctcacccaac    1320
gaaaaattac agaatataaa tttggcaatg tctccattac ccaccgctga aacgccaaag    1380
ccacttcgaa gtagtgctga ccctgcactc aatcaagaag ttgcattaaa attagaacca    1440
aatccagagt cactggaact ttcttttacc atgccccaga ttcaggatca gacacctagt    1500
ccttccgatg gaagcactag acaaagttca cctgagccta atagtcccag tgaatattgt    1560
ttttatgtgg atagtgatat ggtcaatgaa ttcaagttgg aattggtaga aaacttttt    1620 gctgaagaca cagaagcaaa gaacccattt tctactcagg acacagattt agacttggag    1680
atgttagctg cttatatccc aatggatgat gacttccagt tacgttcctt cgatcagttg    1740
tcaccattag aaagcagttc cgcaagccct gaaagcgcaa gtcctcaaag cacagttaca    1800
gtattccagc agactcaaat acaagaacct actgctaatg ccaccactac cactgccacc    1860
actgatgaat taaaaacagt gacaaaagac cgtatggaag acattaaaat attgattgca    1920
tctccatctc ctacccacat acataaagaa actactagtg ccacatcatc accatataga    1980
gatactcaaa gtcggacagc ctcaccaaac agagcaggaa aaggagtcat agaacagaca    2040
gaaaaatctc atccaagaag ccctaacgtg ttatctgtcg ctttgagtca agaactaca    2100 gttcctgagg aagaactaaa tccaaagata ctagctttgc agaatgctca gagaaagcga    2160
aaaatggaac atgatggttc actttttcaa gcagtaggaa ttggaacatt attacagcag    2220
ccagacgatc atgcagctac tacatcactt tcttggaaac gtgtaaaagg atgcaaatct    2280
agtgaacaga atggaatgga gcaaaagaca attattttaa taccctctga tttagcatgt    2340
agactgctgg ggcaatcaat ggatgaaagt ggattaccac agctgaccag ttatgattgt    2400
gaagttaatg ctcctataca aggcagcaga aacctactgc agggtgaaga attactcaga    2460
gctttggatc aagttaactg a                                              2481
```

<210> SEQ ID NO 6
<211> LENGTH: 826
<212> TYPE: PRT
<213> ORGANISM: Artificial Sequence
<220> FEATURE:
<223> OTHER INFORMATION: Human HIF-1 alpha with P to A substitutions

<400> SEQUENCE: 6

```
Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30
```

-continued

```
Glu Ser Glu Val Phe Tyr Glu Leu Ala His Gln Leu Pro Leu Pro His
             35                   40                  45
Asn Val Ser Ser His Leu Asp Lys Ala Ser Val Met Arg Leu Thr Ile
 50                      55                  60
Ser Tyr Leu Arg Val Arg Lys Leu Leu Asp Ala Gly Asp Leu Asp Ile
 65                  70                  75                  80
Glu Asp Asp Met Lys Ala Gln Met Asn Cys Phe Tyr Leu Lys Ala Leu
                 85                  90                  95
Asp Gly Phe Val Met Val Leu Thr Asp Gly Asp Met Ile Tyr Ile
                 100                 105                 110
Ser Asp Asn Val Asn Lys Tyr Met Gly Leu Thr Gln Phe Glu Leu Thr
             115                 120                 125
Gly His Ser Val Phe Asp Phe Thr His Pro Cys Asp His Glu Glu Met
         130                 135                 140
Arg Glu Met Leu Thr His Arg Asn Gly Leu Val Lys Lys Gly Lys Glu
145                 150                 155                 160
Gln Asn Thr Gln Arg Ser Phe Phe Leu Arg Met Lys Cys Thr Leu Thr
                 165                 170                 175
Ser Arg Gly Arg Thr Met Asn Ile Lys Ser Ala Thr Trp Lys Val Leu
             180                 185                 190
His Cys Thr Gly His Ile His Val Tyr Asp Thr Asn Ser Asn Gln Pro
         195                 200                 205
Gln Cys Gly Tyr Lys Lys Pro Pro Met Thr Cys Leu Val Leu Ile Cys
     210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
                 245                 250                 255
Glu Arg Ile Thr Glu Leu Met Gly Tyr Glu Pro Glu Glu Leu Leu Gly
             260                 265                 270
Arg Ser Ile Tyr Glu Tyr Tyr His Ala Leu Asp Ser Asp His Leu Thr
         275                 280                 285
Lys Thr His His Asp Met Phe Thr Lys Gly Gln Val Thr Thr Gly Gln
     290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
                 325                 330                 335
Cys Val Asn Tyr Val Val Ser Gly Ile Ile Gln His Asp Leu Ile Phe
             340                 345                 350
Ser Leu Gln Gln Thr Glu Cys Val Leu Lys Pro Val Glu Ser Ser Asp
         355                 360                 365
Met Lys Met Thr Gln Leu Phe Thr Lys Val Glu Ser Glu Asp Thr Ser
     370                 375                 380
Ser Leu Phe Asp Lys Leu Lys Lys Glu Pro Asp Ala Leu Thr Leu Leu
385                 390                 395                 400
Ala Ala Ala Ala Gly Asp Thr Ile Ile Ser Leu Asp Phe Gly Ser Asn
                 405                 410                 415
Asp Thr Glu Thr Asp Asp Gln Gln Leu Glu Glu Val Pro Leu Tyr Asn
             420                 425                 430
Asp Val Met Leu Pro Ser Pro Asn Glu Lys Leu Gln Asn Ile Asn Leu
         435                 440                 445
Ala Met Ser Pro Leu Pro Thr Ala Glu Thr Pro Lys Pro Leu Arg Ser
```

```
            450                 455                 460
Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
                515                 520                 525

Asn Glu Phe Lys Leu Glu Leu Val Glu Lys Leu Phe Ala Glu Asp Thr
530                 535                 540

Glu Ala Lys Asn Pro Phe Ser Thr Gln Asp Thr Asp Leu Asp Leu Glu
545                 550                 555                 560

Met Leu Ala Ala Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
                595                 600                 605

Glu Pro Thr Ala Asn Ala Thr Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
                675                 680                 685

Asn Val Leu Ser Val Ala Leu Ser Gln Arg Thr Thr Val Pro Glu Glu
                690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
                740                 745                 750

Lys Arg Val Lys Gly Cys Lys Ser Ser Glu Gln Asn Gly Met Glu Gln
                755                 760                 765

Lys Thr Ile Ile Leu Ile Pro Ser Asp Leu Ala Cys Arg Leu Leu Gly
                770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
                820                 825
```